(12) United States Patent
Morris et al.

(10) Patent No.: US 6,897,040 B2
(45) Date of Patent: May 24, 2005

(54) METHODS AND HOST CELLS FOR IMPROVED CELL CULTURE

(75) Inventors: Arvia E. Morris, Seattle, WA (US); Pranhitha Reddy, Seattle, WA (US)

(73) Assignee: Immunex Corporation, Seattle, WA (US)

(*) Notice: Subject to any disclaimer, the term of this patent is extended or adjusted under 35 U.S.C. 154(b) by 148 days.

(21) Appl. No.: 10/109,971

(22) Filed: Mar. 29, 2002

(65) Prior Publication Data

US 2002/0160455 A1 Oct. 31, 2002

Related U.S. Application Data

(62) Division of application No. 09/648,667, filed on Aug. 25, 2000, now Pat. No. 6,413,744.
(60) Provisional application No. 60/150,645, filed on Aug. 25, 1999, provisional application No. 60/168,948, filed on Dec. 3, 1999, and provisional application No. 60/171,949, filed on Dec. 23, 1999.

(51) Int. Cl.[7] .................. C12N 15/00; C12N 15/85; C12N 15/09; C12N 1/19; C12P 21/00
(52) U.S. Cl. ................. 435/69.1; 435/325; 435/358; 435/360; 435/455; 435/254.2; 435/70.1; 435/69.7
(58) Field of Search .................... 435/325, 254.2, 435/70.1, 71.1, 440, 69.1

(56) References Cited

U.S. PATENT DOCUMENTS

| | | | |
|---|---|---|---|
| 5,597,719 A | * | 1/1997 | Freed et al. ............. 435/194 |
| 5,605,690 A | | 2/1997 | Jacobs et al. |
| 5,663,314 A | | 9/1997 | Seger et al. |
| 6,232,117 B1 | | 5/2001 | Mather |
| 6,235,498 B1 | | 5/2001 | Mather et al. |
| 6,413,744 B1 | * | 7/2002 | Morris et al. ............. 435/69.1 |

FOREIGN PATENT DOCUMENTS

| | | |
|---|---|---|
| EP | 0496453 A1 | 7/1992 |
| EP | 0666312 A1 | 8/1995 |
| WO | WO 93/20200 | 10/1993 |
| WO | WO 97/05240 | 2/1997 |
| WO | WO 99/16887 | 4/1999 |

OTHER PUBLICATIONS

Alessandrini et al. J. Biol. Chem., 1996, 271(49): 31612–18.*
Ahmed et al. PNAS, 1997, 94:3627–32.*
Skorski et al. EMBO, 1997, 16:6151–61.*
Alessi et al., "Mechanism of Activation of Protein Kinase B By Insulin and IGF–1," *The EMBO Journal* 15(23):6541–6551, 1996.
Bailey, J. E. et al., "Inverse Metabolic Engineering: A Strategy for Directed Genetic Engineering of Useful Phenotypes," *Biotechnology and Bioengineering,* 52:109–121, 1996.

Brott, B. K. et al., "MEK2 Is a Kinase Related to MEK1 and Is Differentially Expressed in Murine Tissues," *Cell Growth & Differentiation,* 4:921–929, 1993.
Butler, A. A. et al., "Insulin–like growth factor–I receptor signal transduction: at the interface between physiology and cell biology," *Comparative Biochemistry and Physiology, Part B,* 121:19–26, 1998.
Coffer, P. J. et al, "Protein kinase B (c–Akt): a multifunctional mediator of phosphatidylinositol 3–kinase activation," *Biochem. J.,* 335:1–13, 1998.
Datta, S. R. et al., "Cellular survival: a play in three Akts," *Genes & Development,* 13(22):2905–2927.
Furlanetto, R. W. et al., "14–3–3 Proteins interact with the insulin–like growth factor receptor but not the insulin receptor," *Biochem. J.,* 327:765–771, 1997.
Fussenegger, M. and Bailey, J. E., "Control of Mammalian Cell Proliferation as an Important Strategy in Cell Culture Technology, Cancer Therapy and Tissue Engineering," *Cell Engineering,* Mohamed Al–Rubeai, ed., Kluwer Academic, Dordrecht, Boston, London, 1999, pp. 186–219.
Fussenegger, M. and Bailey, J. E., "Molecular Regulation of Cell–Cycle Progression and Apoptosis in Mammalian Cells: Implications for Biotechnology," *Biotechnol. Prog.,* 14(6):807–833, 1998.
Fussenegger, M. and Bailey, J. E., "Genetic optimization of recombinant glycoprotein production by mammalian cells," *Tibech,* 17:35–42, 1999.
Galetic, I. et al., "Mechanism of Protein Kinase B Activation by Insulin/Insulin–Like Growth Factor–1 Revealed by Specific Inhibitors of Phosphoinositide 3–Kinase—Significance for Diabetes and Cancer," *Pharmacol. Ther.,* 82(2–3):409–425, 1999.
Greulich, H. and Erikson, R. L., "An Analysis of Mek1 Signaling in Cell Proliferation and Transformation," *The Journal of Biological Chemistry,* 273(21):13280–13288, 1998.
Hannigan, G. E. et al., "Regulation of cell adhesion and anchorage–dependent growth by a new $\beta_1$–integrin–linked protein kinase," *Nature,* 379:91–96, 1996.
Hsu, S. Y. et al., "Interference of BAD (Bcl–xL/Bcl–2–Associated Death Promoter)—Induced Apoptosis in Mammalian Cells by 14–3–3 Isoforms and P11," *Molecular Endocrinology,* 11(12):1858–1865, 1997.
Klippel, A. et al., Membrane Localization of Phosphatidylinositol 3–Kinase is Sufficient to Activate Multiple Signal–Transducing Kinase Pathways, *Molecular and Cellular Biology,* 16(8):4117–4127, 1996.

(Continued)

*Primary Examiner*—Gerry Leffers
*Assistant Examiner*—Ramin Akhavan
(74) *Attorney, Agent, or Firm*—Kathleen Fowler

(57) ABSTRACT

The invention provides improved methods of recombinant protein production in cell culture. More specifically, the invention relates to the modulation of the IGF-1 signaling pathway in cells so as to improve production characteristics.

32 Claims, 11 Drawing Sheets

OTHER PUBLICATIONS

Konishi, H. et al., "Opposing Effects of Protein Kinase C δ and Protein Kinase B α on $H_2O_2$–Induced Apoptosis in CHO Cells," *Biochemical and Biophysical Research Communications, 264*:840–846, 1999.

Lee, K. H. et al., "Deregulated Expression of Cloned Transcription Factor E2F–1 in Chinese Hamster Ovary Cells Shifts Protein Patterns and Activates Growth in Protein–Free Medium," *Biotechnology and Bioengineering, 50*:273–279, 1996.

Le Gall, M. et al., "The p42/p44 MAP kinase pathway prevents apoptosis induced by anchorage and serum removal," *Molecular Biology of the Cell, 11(3)*:1103–1112, 2000.

Lopaczynski, W., "Differential regulation of signaling pathways for insulin and insulin–like growth factor I," *Acta Biochimica Polonica, 46(1)*:51–60, 1999.

Madrid, L.V., et al., "Akt Suppresses Apoptosis by Stimulating the Transactivation Potential of the RelA/p65 Subunit of NK–κB," *Molecular and Cellular Biology 20(5)*:1626–1638 (2000).

Mueckler, M., "Facilitative glucose transporters," *Eur. J. Biochem., 219*:713–725, 1994.

O'Connor, R. et al., "Identification of Domains of the Insulin–Like Growth Factor I Receptor That Are Required for Protection from Apoptosis," *Molecular and Cellular Biology, 17(1)*:427–435, 1997.

Owaki, H. et al., "Extracellular Signal–Regulated Kinases in T Cells: Characterization of Human ERK1 and ERK2 cDNAs [1,2]," *Biochemical and Biophysical Research Communications, 182(3)*:1416–1422, 1992.

Ozes, O. N. et al., "NF–κ B activation by tumour necrosis factor requires the Akt serine–threonine kinase," *Nature, 401*:82–85, 1999.

Pages, G. et al., "Constitutive mutant and putative regulatory serine phosphorylation site of mammalian MAP kinase kinase (MEK 1)," *EMBO Journal, 13(13)* :3003–3010, 1994.

Pak, S. C. O. et al., "*Super–CHO*—A cell line capable of autocrine growth under fully defined protein–free conditions," *Cytochnology, 22*:139–146, 1996.

Paul, A. et al., "Stress–activated Protein Kinases: Activation, Regulation and Function," *Cell. Signal., 9(6)*:403–410, 1997.

Pelech, S. L., "MAP kinase–dependent pathways in cell cycle control," *Prog. Cell Cycle Res., 1*:33–52, 1995, Abstract.

Rasmussen, B. et al., "Isolation, characterization and recombinant protein expression in Veggie–CHO: A serum–free CHO host cell line," *Cytotechnology, 28*:31–42, 1998.

Romashkova, J. A. and Makarov, S. S, "NF–κB is a target of AKT in anti–apoptotic PDGF signalling," *Nature, 401*:86–89, 1999.

Samadder, P. and Arthur, G., "Decreased Sensitivity to 1–O–Octadecyl–2–O–methyl–glycerophosphocholine in MCF–7 Cells Adapted for Serum–free Growth Correlates with Constitutive Association of Raf–1 with Cellular Membranes," *Cancer Research, 59*:4808–4815, 1999.

Tang, Y. et al., "The Akt proto–oncogene links Ras to Pak and cell survival signals," *Journal of Biological Chemistry, 275(13)*:9106–9109, 2000, Abstract.

Waters, S. B. and Pessin, J. E., "Insulin receptor substrate 1 and 2 (IRS1 and IRS2): what a tangled web we weave," *Cell Biology, 6*:1–4, 1996.

Woessmann, W. et al., "An essential role for mitogen–activated protein kinases, ERKs, in preventing heat–induced cell death," *Journal of Cellular Biochemistry, 74(4)*:648–662, 1999, Abstract.

Yip–Schneider, M. T. et al., "Lack of elevated MAP kinase (Erk) activity in pancreatic carcinomas despite oncogenic K–ras expression," *International Journal of Oncology, 15(2)*:271–279, 1999, Abstract.

Zanghi, J. A. et al., "Serum Protects Protein–Free Competent Chinese Hamster Ovary Cells Against Apoptosis Induced by Nutrient Deprivation in Batch Culture," *Biotechnology and Bioengineering, 64(1)*:108–120, 1999.

\* cited by examiner

SEQUENCE LISTING

<160> NUMBER OF SEQ ID NOS: 10

<210> SEQ ID NO 1
<211> LENGTH: 31
<212> TYPE: DNA
<213> ORGANISM: Artificial Sequence
<220> FEATURE:
<223> OTHER INFORMATION: Description of Artificial Sequence: synthetic
    DNA primer

<400> SEQUENCE: 1
ttgcggccgc atgaacgacg tagccattgt g          31

<210> SEQ ID NO 2
<211> LENGTH: 31
<212> TYPE: DNA
<213> ORGANISM: Artificial Sequence
<220> FEATURE:
<223> OTHER INFORMATION: Description of Artificial Sequence: synthetic
      DNA primer

<400> SEQUENCE: 2
aataatgcgg ccgctcaggc tgtgccactg g                          31

<210> SEQ ID NO 3
<211> LENGTH: 35
<212> TYPE: DNA
<213> ORGANISM: Artificial Sequence
<220> FEATURE:
<223> OTHER INFORMATION: Description of Artificial Sequence: synthetic
      DNA primer

<400> SEQUENCE: 3
ggatccgccg ccaccatgcc caagaagaag ccgac                      35

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence: synthetic
      DNA primer

<400> SEQUENCE: 4
ctggagtctc tcgggcgaca tgtat                                 25

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: synthetic
      DNA primer

<400> SEQUENCE: 5
cccgagagac tccaggggac t                                     21

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: synthetic
      DNA primer

<400> SEQUENCE: 6
gcggccgctc agatgctagc ggcatgggtt                            30

<210> SEQ ID NO 7
<211> LENGTH: 84
<212> TYPE: DNA
<213> ORGANISM: Artificial Sequence
<220> FEATURE:
<223> OTHER INFORMATION: Description of Artificial Sequence: synthetic
      DNA primer

<400> SEQUENCE: 7
cccgggccgc caccatgggg agtagcaaga gcaagcctaa ggaccccagc cagcgcaacg     60

-continued

```
acggggctga ggagatggag gtgt                                          84

<210> SEQ ID NO 8
<211> LENGTH: 31
<212> TYPE: DNA
<213> ORGANISM: Artificial Sequence
<220> FEATURE:
<223> OTHER INFORMATION: Description of Artificial Sequence: synthetic
      DNA primer

<400> SEQUENCE: 8
aataatgcgg ccgctcaggc tgtgccactg g                                  31

<210> SEQ ID NO 9
<211> LENGTH: 34
<212> TYPE: DNA
<213> ORGANISM: Artificial Sequence
<220> FEATURE:
<223> OTHER INFORMATION: Description of Artificial Sequence: synthetic
      DNA primer

<400> SEQUENCE: 9
ccaccatcta gatcactgtt ccgaagtgac aggt                               34

<210> SEQ ID NO 10
<211> LENGTH: 51
<212> TYPE: DNA
<213> ORGANISM: Artificial Sequence
<220> FEATURE:
<223> OTHER INFORMATION: Description of Artificial Sequence: synthetic
      DNA primer

<400> SEQUENCE: 10
ccccaagctt gtcgacgccg ccaccatgga gcaacaggat cagagcatga a            51
```

US 6,897,040 B2

METHODS AND HOST CELLS FOR IMPROVED CELL CULTURE

RELATED APPLICATIONS

This application is a divisional of U.S. patent application Ser. No. 09/648,667 filed Aug. 25, 2000, issued as U.S. Pat. No. 6,413,744, and claims the benefit of U.S. Provisional Applications Ser. No. 60/150,645 filed Aug. 25, 1999, Ser. No. 60/168,948 filed Dec. 3, 1999, and Ser. No. 60/171,949 filed Dec. 23, 1999, the disclosures of which are incorporated by reference in their entirety.

FIELD OF THE INVENTION

The invention is in the field of eukaryotic cell culture, and improved methods of recombinant protein production. More specifically, the invention relates to the modulation of the IGF-1 signaling pathway in cultured eukaryotic cells so as to obtain cell lines that can be used in serum-free and/or protein-free and/or peptone-free media.

BACKGROUND OF THE INVENTION

Serum is often used for the propagation of mammalian cell lines. However, when mammalian cells are used for the production of recombinant proteins, there is increasing pressure to remove serum from the manufacturing process. Some of the driving reasons to implement serum-free cell-culture technology are the expense of serum, variation between serum lots and serum quality, regulatory concerns regarding biological agents in serum and the burden of removing serum proteins in downstream processing. (Adamson R., 1994, Ann. Hematol. 68 Suppl 3: S9-14; Thomas et al., *Animal Cell Technology: Products of Today, Prospects for Tomorrow* (Spier R E, Griffiths J B & Berthold W (ed.) pp. ESACT Butterworth-Heinemann, 1994)). There is also a recognized need in the art, for reasons of reduced cost and increased media consistency, for production cell lines able to grow in medium free of peptone additives. In addition, peptide growth factors are one of the most expensive media components; removal of such growth factors achieves significant cost reduction.

Adaptation of recombinant production cell lines to serum-free growth can be a time consuming step in process development with variable effects on recombinant protein expression and protein quality (Barnes et al., 1980, Anal. Biochem. 102: 255–270; Evans et al., 1956, Cancer Res. 16: 77–86; Hamilton et al., 1977, In Vitro 13: 537–547; Sinacore et al., 1996, Biotech. Bioeng. 52:518–528). For example, CHO cell lines have been adapted by Gandor et al. to growth in medium free not only of serum and growth factors (such as insulin) but of all proteins (Gandor et al. 1995, FEBS Lett. 377: 290–294). With this adaptation, however, came difficulties caused by cell line reversion. The cells, which were initially DHFR-negative, reverted to a DHFR-positive phenotype during prolonged continuous culture in the serum-free medium. Other investigators found that previously adapted serum-free cultures reverted to serum-dependent phenotype when cultured in serum-containing media (Yao et al., 1991, Proc Natl Acad Sci USA 88: 9422–9425).

Another cell line, termed "Veggie-CHO," was adapted to be able to grow in serum-free and protein-free medium while still being DHFR deficient (Rasmussen et al., 1998, Cytotechnology 28:31–42). The adaptation process involved the gradual reduction of serum supplementation in the media and the replacement of serum with low levels of growth factors, IGF-1 and transferrin, in an enriched cell growth medium. The cells grown in serum-free medium were then weaned off these growth factors. Veggie-CHO cells have been shown to maintain an average doubling time of 22 hours in continuous growth cultures over a period of three months and have retained the DHFR-deficient phenotype of their parental DXB11-CHO cells (Id.). However, the process of achieving Veggie-CHO was time consuming and required over 160 passages. Additionally, there was an enormous difference in the cellular response (as measured by viability and doubling time) to growth in medium with low concentrations of serum and growth in medium with no serum. Only by making a gradual transition to medium without serum, with a prolonged adaptation period, were viable and stable (DHRF-) cell lines obtained.

One method that has been proposed to generate cell lines that can grow in media with reduced cytokines, hormones and growth factors is to cause the cells to express a bcl-2 gene (WO 93/20200 by Evan et al.). Evan et al. reported that if one took myeloma/hybridoma cells (which were chosen as cells that express essentially no bcl-2 mRNA or protein), and introduced into them a bcl-2 expression construct, the resulting cell lines had more stress resistance and decreased requirements for fetal calf serum (Id.). However, complete removal of serum and growth factors from the medium in which the hybridoma cells were grown was not reported (Id.). In another study that was directed to analyzing the signaling of the kinase MEK1, Greulich and Erickson transfected NIH-3T3 cells with an expression vector encoding for a fusion protein containing a constitutively activated MEK1 mutant (termed DD) fused to the hormone-binding domain of the estrogen receptor (encoding a product termed "Mek-ER") (Greulich et al., 1998, J. Biol. Chem. 273:13280–13288). Addition of the synthetic ligand 4-hydroxytamoxifen presumably activated Mek-ER. These authors reported that in the presence of 4-hydroxytamoxifen, the Mek-ER expressing cells could proliferate in low (0.5%) serum (Id.). However, when the cells were grown in medium without 4-hydroxytamoxifen but with 10% serum, they proliferated three times as fast. Thus, they concluded that expression of MEK1 could not override the requirement for serum and growth factors in these cells.

Yet another cell line adapted to growth in medium free of both serum and growth factors has been termed "Super CHO" (Pak et al., 1996, Cytotechnology 22:139–146; see also WO 97/05240). In order to overcome the need for exogenously added growth factor, expression vectors containing the genes for transferrin and IGF-1 were transfected into CHO cells (Id.). In addition, EP 0 666 312 describes a method of generating cell cultures that can proliferate in serum-free and protein-free medium by transfecting cells with an expression vector that encodes the cell-cycle regulatory proteins cyclin E and/or transcription factor E2F-1.

Although many technical advances have been made, there still remains a need in the art to rapidly, and reliably, generate industrially important cell cultures that can proliferate in serum-free and/or protein-free and/or peptone-free media. The present invention is directed at fulfilling this need.

SUMMARY OF THE INVENTION

The invention is based, in part, on the discovery that cells that have been adapted over many generations to growth in serum-free and protein-free medium, Veggie-CHO cells, have alterations in the intracellular IGF-1 receptor signaling cascade. The present inventors found that the advantageous phenotypes of the Veggie-CHO cells could be duplicated in a more controlled, consistent and reliable manner by genetically engineering individual components of the IGF-1 signaling pathways.

Accordingly, in one aspect, the invention provides an eukaryotic host cell genetically engineered to express a gene for a protein of interest and at least one IGF-1-signaling pathway gene. Preferred IGF-1-signaling pathway genes are a PKB gene (e.g., PKBα, PKBβ, and PKBγ), a MEK gene (e.g., MEK1 and MEK2), a glut5 gene, a glut1 gene, an ERK gene (e.g., ERK1, also known as MAPK p44, and ERK2, also known as MAPK p42), a JNK gene, a 14-3-3 protein gene, a PDK gene, an IRS gene, and a P13 kinase gene. The protein of interest can be any recombinant protein of economic interest. Examples of such proteins include but are not limited to a soluble TNF receptor, a soluble IL-4 receptor, a soluble IL-1 type II receptor, a soluble Flt3 ligand, a soluble CD40 ligand, an erythropoeitin, an antibody, and hormones, to name just a few. Optionally, the gene for the protein of interest and/or the IGF-1-signaling pathway gene(s) can be linked to a selectable marker. Preferred host cells are mammalian cells, and more preferably mammalian cells that are grown in culture. In addition, the host cell can be adapted to grow in serum-free and/or protein-free and/or peptone-free medium.

In another related aspect, the invention provides a method of producing a protein of interest, the method comprising culturing an eukaryotic host cell genetically engineered to express a gene for a protein of interest and at least one IGF-1-signaling pathway gene under conditions such that the protein of interest is expressed. Optionally, the method entails collecting and/or purifying the protein of interest from the cell culture. Such methods are particularly advantageous for culturing the host cells in serum-free and/or growth-factor free and/or protein-free and/or peptone-free media. In addition, the methods of the invention frequently improved yields of the protein of interest.

In still another aspect, the invention relates to a method of producing a cell for production of a protein of interest, the method comprising genetically engineering a cell to express a gene that encodes a protein of interest, and to express an IGF-1-signaling pathway gene. The cells can be genetically engineered in any order or simultaneously.

Another aspect of the invention is a method of producing a mammalian cell line capable of growth in serum-free medium, the method comprising exposing cells that have been genetically engineered to overexpress or underexpress at least one IGF-1-signaling pathway gene to serum-free medium, and isolating a cell line that grows in serum-free medium. In alternative or additional embodiments, the cells are exposed to protein-free and/or peptone-free medium, and cell lines that grow in protein-free and/or peptone-free medium are isolated. Preferred IGF-1-signaling pathway genes are MEK genes, MAP kinase genes, and PKB genes.

BRIEF DESCRIPTION OF THE FIGURES

FIG. 1.

FIG. 2. Production by PKB, control pools and parental cells in media containing peptone and IGF-1.

FIG. 3. Production by PKB, control pools and parental cells in peptone and IGF-1 free conditions.

FIG. 5. Western blots of MAPK and MEK1 in 2A5-3 cells transfected with MEK1 expression plasmids and in control cells.

FIG. 6A demonstrates the % viability of the adapted pools over time. FIG. 6B demonstrates the average growth rate of the pools over time.

DETAILED DESCRIPTION OF THE INVENTION

Figure 1A:
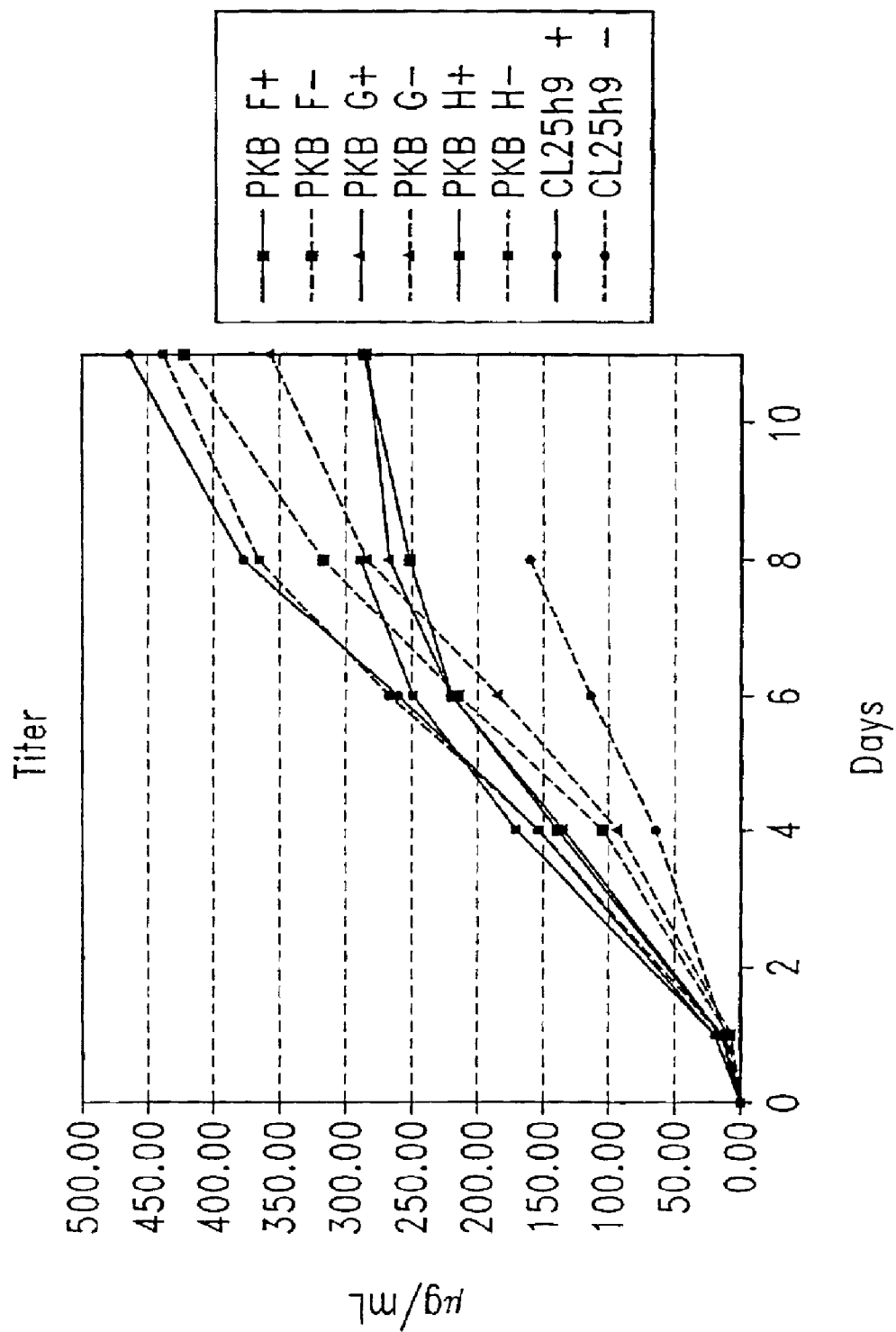
FIGS. 1A and 1B compare the performance (titer of protein of interest and viability, respectively) of PKB pools (F, G and H) to the parental cell line (25H9) in production conditions with IGF-1 (F+, G+ and H+; also designated with solid lines) and without IGF-1 (F−, G− and H−; also designated with dotted line).

Numerous extracellular molecules modulate the cellular functions of eukaryotic cells via binding to membrane receptors on the cell surface; the actions of these extracellular molecules are in turn mediated by signaling mechanisms (Coffer et al., 1998, Biochem J. 335:1–13). Some cell activities are mediated by IGF-1 signaling mechanisms (Thomas et al., 1994; Butler et al., 1998, Comparative Biochemistry and Physiology, Part B 121:19–26). The invention is based, in part, on the discovery that although Veggie-CHO cells do not upregulate levels of endogenous IGF-1 or insulin, these cells have more IGF-1 receptors than either DXB11 CHO, or CHO cells adapted to growth in serum-free medium. In addition, in the absence of IGF-1, phosphorylation of the IGF-1 receptor is not up regulated in Veggie CHO cells. However, when grown in growth medium lacking IGF-1, Veggie CHO cells have an increase in basal phosphorylation of PKB and MAPK compared to CHO cells grown in serum, or to CHO cells adapted to serum-free medium with IGF-1. Moreover, when IGF-1 is added to the growth media, PKB and MAPK become hyperphosphorylated. This increased sensitivity to IGF-1 and the absence of overexpression of endogenous IGF-1 in the cells themselves indicate that Veggie-CHO cell lines have altered intracellular IGF-1-signaling.

Thus, in one embodiment of the instant invention, cell lines with advantageous properties similar to those of Veggie-CHO cell lines (e.g., with increased ability to grow in medium lacking serum, growth-factors and/or peptone) are created by genetically engineering cell lines to express one or more IGF-1-signaling pathway gene(s). For example, for an IGF-1-signaling pathway gene whose upregulation activates the IGF-1-signaling pathway, cells are genetically engineered to express higher levels and/or constitutively activated IGF-1-signaling pathway gene products. Alternatively, for an IGF-1-signaling pathway gene whose downregulation leads to ability to grow in medium lacking serum, growth-factors and/or peptone, cells are genetically engineered to either reduce or knock out expression, or to express mutant (e.g., dominant mutant) forms of the IGF-1-signaling pathway gene products.

For purposes of the invention, an "IGF-1-signaling pathway gene" excludes the genes encoding growth factors themselves such as IGF-1 and insulin, as well as the genes for cell cycle regulated transcription factors and mitochondrial proteins such as bcl-2. Instead, the invention relates to the manipulation of the intracellular machinery described below that normally responds to extracellular IGF-1 as part of a cytoplasmic kinase cascade mechanism. IGF-1 receptor signal transduction is reviewed in Butler et al., 1998, supra.

One IGF-1-signaling pathway involves activation of phosphatidylinositol 3-kinase (PI-3K), which results in the generation of a membrane restricted second messenger, polyphosphatidylinositide containing a 3'-phosphate (Coffer et al., 1998, supra). IGF-1-signaling components involved in the PI-3K signaling pathway include the IGF-1 receptor, IRSs, PKBs, PKB phosphatase, PI-3K, and PDKs. Another signaling pathway of IGF-1 involves the activation of p21-MAPK. Signaling components involved in this pathway include MEK, RAF, and MAPK (including ERK1, aka p44 MAPK, and ERK2, aka p42 MAPK). As another response to IGF-1-signaling, cells also upregulate the number of sugar transporters, e.g., glut1 and glut4 on the cell surface. In the present invention, these various IGF-1-signaling pathway gene products are modulated by genetically engineering the cells in the appropriate manner. Modulation of a signaling component(s) includes mutating and/or overexpressing or upregulating and/or underexpressing or downregulating the gene(s) encoding the component(s).

IGF-1-signaling pathway genes that are advantageously upregulated in the compositions and methods of the invention include the IGF-1 receptor (Genbank Accession No. NM 000875; Ullrich et al., 1986, EMBO J. 5:2503–12; reviewed in LeRoith et al., 1995, Endocr. Rev. 16:143–164) (particularly the β subunit which contains the tyrosine kinase domain and interacts with downstream signaling molecules), PKBs (PKBα, PKBβ and PKBγ; reviewed in Coffer et al., 1998), the MEKs (MEK1 and MEK2; see for example Pages et al., 1994, EMBO J. 13:3003–3010, which describes the sequence encoding hamster MEK1, and Brott et al., 1993, Cell Growth Different. 4:921 and Genbank Accession No. S68267, which describes murine MEK2), the MAPKs (including p38, Han et al., 1994, Science 265:808–811, Genbank Accession No. L35253; and particularly p44/ERK1 and p42/ERK2, described in Owaki et al. BBRC 1992:1416), JNK1 (e.g., the murine sequence described at Genbank Accession No. AB005663) JNK2 (e.g., the human sequence described at Genbank Accession No. L31951; Sluss et al., 1994, Mol. Cell. Biol. 14:8376–8384) JNK3 (e.g., the murine sequence described at Genbank Accession No. AB005665), 14-3-3 protein (Yu et al., 1997, Mol. Endocrinol. 11:1858), IRS-1 (Genbank Accession No. L24563; Araki et al., 1994, Biochim. Biophys. Acta. 1221:353–6; Sun et al., 1991, Nature 352:73–77), IRS-2 (Genbank Accession No. AF073310; Vassen et al., 1999, Mol. Endocrinol. 13:485–494; the IRS proteins are also reviewed in Waters and Pessin, 1996, Trends Cell Biol. 6:1), BAD (e.g., the murine sequence described at Genbank Accession No. L37296; Yank et al., 1995, Cell 80:285–291), P13 kinase (reviewed in Kapeller and Cantley, 1994, BioEssays 16:565; see also, for example, Escobedo et al., 1991, Cell 65:75–82 for a describing the sequence which encodes the 85 kd subunit, and Ruis et al., 1992, Cell 70:419–429, describing the sequence which encodes the 110 kd subunit), PDK1 (e.g., Genbank Accession Nos. AF086625 (murine) and AF017995 (human); also reviewed in Galetic et al., 1999, Pharmacol Ther. 82:409–25) and PDK2 (e.g., Genbank Accession Nos. U40282 and NM004517). As shown by the experimental data reported herein, upregulation of PKB, ERK1, ERK2 and MEK1 are particularly preferred because these are the proteins found to be upregulated (as measured by hyperphosphorylation) in the Veggie CHO cells that were adapted over many generations to growth in serum-free, protein-free medium. In addition, upregulation of sugar transporters such as glut1 and glut5 are also preferred (Mueckler, 1994, Eur. J. Biochem. 219:713–725). IGF-1-signaling pathway genes that are advantageously downregulated in the compositions and methods of the invention include BAD, gsk3 (e.g., Genbank Accession No. NM-002093; Stambolic and Woodgett, 1994, Biochem. J. 303:701–704), and phosphatases that dephosphorylate any of the proteins, or their substrates, that are advantageously upregulated.

In one embodiment of the instant invention, cells are genetically engineered to overexpress a PKB gene so as to generate cells that are more easily adapted to growth and/or production in serum-free and/or peptone-free and/or growth factor free medium. Mammalian genomes contain three genes encoding PKBs (reviewed in Coffer et al., 1998, Biochem. J. 335:1–13), termed PKBα, PKBβ, and PKBγ, which can be used in the practice of the invention. In one non-limiting example of the invention described below, overexpression of PKBα in CHO cells expressing the recombinant protein IL-1R II improved the viability of the cells under production conditions. Cells transfected with a PKB expression vector which were grown without IGF-1 added to the production medium had similar viabilities to control cells transfected with empty vector which were grown with IGF-1 in the production medium. In addition, cell pools genetically engineered to overexpress PKB and adapted to grow in medium without IGF-1 or peptones have higher viability and higher levels of protein of the protein of interest than control pools or the parental cell line, C125H9. Thus, the overexpression of PKB in a mammalian production cell allows for successful production runs under serum-free and/or protein-free and/or peptone-free conditions.

In yet another embodiment of the instant invention, MAP Kinase (MAPK) is upregulated within the production cell. As demonstrated herein, phosphorylation of MAPK in Veggie CHO cells is increased at basal levels and is hypersensitive to the addition of IGF-1. Hyperphosphorylation in response to IGF-1 addition may be involved in the IGF-1 independent growth and survival of CHO cells adapted to grow in serum-free, protein-free medium. This change in the phosphorylation state can be the result of an increase in MEK activity in cells adapted to grow in serum-free, protein-free medium.

Thus, in another embodiment of the instant invention, the MEK pathway is upregulated in production cells. Data presented herein by way of non-limiting examples demonstrates that phosphorylation of MAPKs within the cells facilitates their adaptation to growth in serum-free, protein-free medium. As described below, overexpression of MEK1 (including various active forms of MEK1) in DXB 11 cells facilitated the cells' rapid and direct adaptation to serum-free growth, and to growth in serum-free, peptone-free medium. The overexpression of PKB along with MEK does not appear to influence the serum-free adaptation process; however, the doubly transfected cells (MEK/PKB and MEK/myrPKB) can have an advantage in growth in the absence of IGFs and/or peptones. Overexpression of MEK in other serum-dependent cell lines can also facilitate adaptation to serum-free growth.

Thus, yet another aspect of the invention is genetically engineering the cells to modulate two or more of the IGF-1-signaling pathway genes. Thus, the invention includes the upregulation and/or downregulation of any two or more of the above-mentioned IGF-1-signaling pathway genes. This aspect of the invention is illustrated by way of non-limiting examples below, whereby both PKB and MEK1 genes were coexpressed in mammalian cell lines.

In still another embodiment of the invention, cells that can grow in serum-free, protein-free medium are derived by genetically engineering the cells to constituently express a sugar transporter on the surface of the cell. The IGF-1 signaling pathway usually causes the glucose 1 (glut1) transporter to be upregulated on the cell surface. Subsequently, glucose uptake is increased and the cell metabolism is upregulated (Coffer et al., 1998, supra). Sugar transporter genes for which the cells can be genetically engineered to upregulate include but are not limited to the glut1 gene and the glut5 gene. As described below in a non-limiting embodiment of the instant invention, CHO cells were transfected with an expression vector that directs the overexpression of the glucose 5 (glut5) transporter gene. The transfected CHO cells grew in medium containing fructose, and not glucose, as the carbon source. Using fructose allows greater control over the quantity of carbon source used by the cell, and creating less by-products that are toxic to the culture. Furthermore, after a period of adaptation, cells overexpressing the glut5 gene were able to grow in a serum-free, protein-free medium, while cells transfected with a control empty vector were not.

By the term "genetically engineered" is meant any recombinant DNA or RNA method used to create a eukaryotic host cell that expresses a gene at elevated levels, at lowered levels, or a mutant form of the gene. In other words, the cell has been transfected, transformed or transduced with a recombinant polynucleotide molecule, and thereby altered so as to cause the cell to alter expression of a desired protein. Methods and vectors for genetically engineering cells and/or cell lines to express a protein of interest are well known to those of skill in the art; for example, various techniques are illustrated in *Current Protocols in Molecular Biology*, Ausubel et al., eds. (Wiley & Sons, New York, 1988, and quarterly updates) and Sambrook et al., *Molecular Cloning: A Laboratory Manual* (Cold Spring Laboratory Press, 1989). Genetic engineering techniques include but are not limited to expression vectors, targeted homologous recombination and gene activation (see, for example, U.S. Pat. No. 5,272,071 to Chappel) and trans activation by engineered transcription factors (see, for example, Segal et al., 1999, Proc. Natl. Acad. Sci. USA 96(6):2758–63).

Methods of upregulating an IGF-1-signaling pathway gene product include overexpression of the encoded wild-type protein, expression of an altered protein (e.g., partly or constitutively activated mutant), or a genetically engineering the cells to express a protein with an altered cellular distribution (e.g., a myristylated PKB protein which is targeted to the cell membrane, as described below in the examples) that has increased activity. Although overexpression of the IGF-1-signaling pathway gene product is desired, it should be noted that expression of extremely high levels of any gene product, especially IGF-1-signaling pathway gene products, is detrimental or even lethal to a cell, and as such should be avoided. Titration of the appropriate expression level can be manipulated in any of a number of ways (e.g., by choice of promoter or change in gene copy number) and is within the skill of those in the art.

Preferably, the cells are genetically engineered to express an IGF-1-signaling pathway gene product that is homologous to, or derived from the same species, as that of the cell. For example, in the non-limiting embodiments described below, primers based upon the known PKBα and MEK1 coding sequences were used to clone the corresponding sequence from Chinese Hamster Ovary cells, which in turn were used as the expression host. However, as IGF-1-signaling pathway genes tend to be well conserved, it is expected that even expression of heterologous gene products will be advantageous.

Methods of downregulating the expression of an IGF-1-signaling pathway gene product include the use of ribozyme technologies, antisense and triple helix technologies, targeted homologous recombination to knockout or otherwise alter the endogenous gene, and expression of dominant negative mutant forms of the IGF-1-signaling pathway gene product. Such methods of upregulating and/or downregulating the expression of gene products are well known to those of skill in the art.

By a "heterologous regulatory element" is meant a genentically encoded element that affects the transcriptional or translational regulation of a coding sequence operably linked thereto, wherein the element is not normally found in nature associated or operatively linked to the coding sequence. Heterologous regulatory elements can be promoters, enhancer regions, transcriptional initiation sites, transcriptional termination signals (e.g., poly adenylation signals), translational initiation sequences, etc. Promoters can be constitutive promoters (e.g., those derived from housekeeping genes whose transcription rate is relatively constant, or some viral promoters), inducible promoters (e.g., the metallothionin promoter that is induced in the presence of heavy metals), tissue or cell type specific promoters (e.g., the globin promoters) or promoters derived from animal viruses (e.g., those from CMV, SV40, Adenoviral, Herpesvirus, RSV, HIV, etc.). Enhancers typically increase the level of transcription from operatively linked genes. Enhancers can also be constitutive, tissue specific, and/or inducible (e.g., the CMV enhancer, the SV40 enhancer, the HIV TAR enhancer).

Host cells for use in the invention are eukaryotic host cells, and preferably mammalian cells. Preferably, the cells are also genetically engineered to express a gene of interest. Even more preferably, the host cells are mammalian production cells adapted to grow in cell culture. Examples of such cells commonly used in the industry are CHO, VERO, BHK, HeLa, CV1 (including Cos), MDCK, 293, 3T3, myeloma cell lines (especially murine), PC12 and WI38 cells.

Particularly preferred host cells are Chinese hamster ovary (CHO) cells, which are widely used for the production of several complex recombinant proteins, e.g. cytokines, clotting factors, and antibodies (Brasel et al., 1996, Blood 88:2004–2012; Kaufman et al., 1988, J. Biol Chem 263: 6352–6362; McKinnon et al., 1991, J Mol Endocrinol 6:231–239; Wood et al., 1990, J. Immunol 145:3011–3016). The dihydrofolate reductase (DHFR)-deficient mutant cell line (Urlaub et al., 1980, Proc Natl Acad Sci USA 77:4216–4220), DXB11 and DG-44, are the CHO host cell lines of choice because the efficient DHFR selectable and amplifiable gene expression system allows high level recombinant protein expression in these cells (Kaufman R. J., 1990, Meth Enzymol 185:527–566). In addition, these cells are easy to manipulate as adherent or suspension cultures and exhibit relatively good genetic stability. CHO cells and recombinant proteins expressed in them have been extensively characterized and have been approved for use in clinical manufacturing by regulatory agencies.

For purposes of the invention, a gene for a protein of interest is a gene that encodes a protein of pharmaceutical, medicinal, nutritional, and/or industrial value. Particularly preferred proteins of interest are protein-based drugs. Preferably, the proteins of interest are expressed as extracellular products. Proteins of interest that can be produced using the cell culturing methods and compositions of the invention include but are not limited to a Flt3 ligand, a CD40 ligand, erythropoeitin, thrombopoeitin, calcitonin, Fas ligand, ligand for receptor activator of NF-kappa B (RANKL), TNF-related apoptosis-inducing ligand (TRAIL), ORK/Tek, thymic stroma-derived lymphopoietin, granulocyte colony stimulating factor, granulocyte-macrophage colony stimulating factor, mast cell growth factor, stem cell growth factor, epidermal growth factor, RANTES, growth hormone, insulin, insulinotropin, insulin-like growth factors, parathyroid hormone, interferons, nerve growth factors, glucagon, interleukins 1 through 18, colony stimulating factors, lymphotoxin-B, tumor necrosis factor, leukemia inhibitory factor, oncostatin-M, and various ligands for cell surface molecules Elk and Hek (such as the ligands for eph-related kinases, or LERKS). Descriptions of proteins that can be expressed according to the inventive methods may be found in, for example, *Human Cytokines: Handbook for Basic and Clinical Research, Vol. II* (Aggarwal and Gutterman, eds. Blackwell Sciences, Cambridge Mass., 1998); *Growth Factors:A Practical Approach* (McKay and Leigh, eds., Oxford University Press Inc., New York, 1993) and *The Cytokine Handbook* (A W Thompson, ed.; Academic Press, San Diego Calif.; 1991).

Receptors for any of the aforementioned proteins can also be expressed using the inventive methods and compositions, including both forms of tumor necrosis factor receptor (referred to as p55 and p75), Interleukin-1 receptors (type 1 and 2), Interleukin-4 receptor, Interleukin-15 receptor, Interleukin-17 receptor, Interleukin-18 receptor, granulocyte-macrophage colony stimulating factor receptor, granulocyte colony stimulating factor receptor, receptors for oncostatin-M and leukemia inhibitory factor, receptor activator of NF-kappaB (RANK), receptors for TRAIL, and receptors that comprise death domains, such as Fas or Apoptosis-Inducing Receptor (AIR).

Other proteins that can be expressed using the inventive methods and compositions include cluster of differentiation antigens (referred to as CD proteins), for example, those disclosed in *Leukocyte Typing VI* (*Proceedings of the VIth International Workshop and Conference*; Kishimoto, Kikutani et al., eds.; Kobe, Japan, 1996), or CD molecules disclosed in subsequent workshops. Examples of such molecules include CD27, CD30, CD39, CD40; and ligands thereto (CD27 ligand, CD30 ligand and CD40 ligand). Several of these are members of the TNF receptor family, which also includes 41BB and OX40; the ligands are often members of the TNF family (as are 41BB ligand and OX40 ligand); accordingly, members of the TNF and TNFR families can also be expressed using the present invention.

Proteins that are enzymatically active can also be expressed according to the instant invention. Examples include metalloproteinase-disintegrin family members, various kinases, glucocerebrosidase, superoxide dismutase, tissue plasminogen activator, Factor VIII, Factor IX, apolipoprotein E, apolipoprotein A-I, globins, an IL-2 antagonist, alpha-1 antitrypsin, TNF-alpha Converting Enzyme, and numerous other enzymes. Ligands for enzymatically active proteins can also be expressed by applying the instant invention.

The inventive compositions and methods are also useful for expression of other types of recombinant proteins, including immunoglobulin molecules or portions thereof, and chimeric antibodies (i.e., an antibody having a human constant region couples to a murine antigen binding region) or fragments thereof. Numerous techniques are known by which DNA encoding immunoglobulin molecules can be manipulated to yield DNAs capable of encoding recombinant proteins such as single chain antibodies, antibodies with enhanced affinity, or other antibody-based polypeptides (see, for example, Larrick et al., 1989, Biotechnology 7:934–938; Reichmann et al., 1988, Nature 332:323–327; Roberts et al., 1987, Nature 328:731–734; Verhoeyen et al., 1988, Science 239:1534–1536; Chaudhary et al., 1989, Nature 339:394–397).

Various fusion proteins can also be expressed using the inventive methods and compositions. Examples of such fusion proteins include proteins expressed as fusion with a portion of an immunoglobulin molecule, proteins expressed as fusion proteins with a zipper moiety, and novel polyfunctional proteins such as a fusion proteins of a cytokine and a growth factor (i.e., GM-CSF and IL-3, MGF and TL-3). WO 93/08207 and WO 96/40918 describe the preparation of various soluble oligomeric forms of a molecule referred to as CD40L, including an immunoglobulin fusion protein and a zipper fusion protein, respectively; the techniques discussed therein are applicable to other proteins.

However, for purposes of this application, the definition of a gene for a protein of interest excludes genes encoding proteins that are typically used as selectable markers in cell culture such as auxotrophic, antimetabolite and/or antibiotic markers. Nevertheless, the invention does include the use of a selectable marker as an aid in selecting cells and/or amplifying clones that are genetically engineered to express a gene of interest and/or an IGF-1-signaling pathway gene. Preferably, the selectable marker gene is positioned adjacent to the gene of interest and/or an IGF-1-signaling pathway gene such that selection and/or amplification of the marker gene will select and/or amplify the adjacent gene.

Specific examples of genes that encode selectable markers are those that encode antimetabolite resistance such as the DHFR protein, which confers resistance to methotrexate (Wigler et al., 1980, Natl. Acad. Sci. USA 77:3567; O'Hare et al., 1981, Proc. Natl. Acad. Sci. USA 78:1527); the GPT protein, which confers resistance to mycophenolic acid (Mulligan & Berg, 1981, Proc. Natl. Acad. Sci. USA 78:2072), the neomycin resistance marker, which confers resistance to the aminoglycoside G-418 (Colberre-Garapin et al., 1981, J. Mol. Biol. 150:1); the Hygro protein, which confers resistance to hygromycin (Santerre et al., 1984, Gene 30:147); and the Zeocin™ resistance marker (available commercially from Invitrogen). In addition, the herpes simplex virus thymidine kinase (Wigler et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy et al., 1980, Cell 22:817) genes can be employed in tk⁻, hgprt⁻ or aprt⁻ cells, respectively.

Various tissue culture media, including serum-free and/or defined culture media, are commercially available. Tissue culture media is defined, for purposes of the invention, as a media suitable for growth of animal cells, and preferably mammalian cells, in in vitro cell culture. Typically, tissue culture media contains a buffer, salts, energy source, amino acids, vitamins and trace essential elements. Any media capable of supporting growth of the appropriate eukaryotic cell in culture can be used; the invention is broadly applicable to eukaryotic cells in culture, particularly mammalian cells, and the choice of media is not crucial to the invention. Tissue culture media suitable for use in the invention are commercially available from, e.g., ATCC (Manassas, Va.). For example, any one or combination of the following media can be used: RPMI-1640 Medium, Dulbecco's Modified Eagle's Medium, Minimum Essential Medium Eagle, F-12K Medium, Iscove's Modified Dulbecco's Medium. When defined medium that is serum-free and/or peptone-free is used, the medium is usually highly enriched for amino acids and trace elements (see, for example, U.S. Pat. No. 5,122, 469 to Mather et al., and U.S. Pat. No. 5,633,162 to Keen et al.).

The term "serum-free" as applied to media includes any mammalian cell culture medium that does not contain serum, such as fetal bovine serum. The term "insulin-free" as applied to media includes any medium to which no exogenous insulin has been added. By exogenous is meant, in this context, other than that produced by the culturing of the cells themselves. The term "IGF-1-free" as applied to media includes any medium to which no exogenous Insulin-like growth factor-1 (IGF-1) or analog (such as, for example, LongR³-IGF-1, see below) has been added. The term "growth-factor free" as applied to media includes any medium to which no exogenous growth factor (e.g., insulin, IGF-1) has been added. The term "protein-free" as applied to media includes medium free from exogenously added protein, such as, for example, transferrin and the protein growth factors IGF-1 and insulin. Protein-free media may or may not have peptones. The term "peptone-free" as applied to media includes any medium to which no exogenous protein hydrolysates have been added such as, for example, animal and/or plant protein hydrolysates. Peptone-free media has the advantages of lower lot to lot variability and fewer filtration problems than media containing plant or animal hydrolysates. Chemically defined media are media in which every component is defined and obtained from a pure source, preferably a non-animal source.

The following examples are offered by way of illustration, and not by way of limitation. Those skilled in the art will recognize that variations of the invention embodied in the examples can be made, especially in light of the teachings of the various references cited herein, the disclosures of which are incorporated by reference in their entirety.

EXAMPLE 1

Recombinant Cytokine Protein Expression In Veggie-CHO Cells

The Veggie-CHO host (adapted to growth in serum-free medium) and the parental serum-requiring host DXB11-CHO were genetically engineered using the DHFR/MTX selection and gene amplification method to secrete high levels of recombinant Flt3 ligand (McKenna et al., 1995). The Veggie-CHO transfectant pools were selected for growth in 150 nM methotrexate (MTX) to amplify recombinant protein expression. Selection of the Veggie-CHO transfectant pool in MTX levels higher than 150 nm concentration did not result in significant increase in the expression of this cytokine molecule. The DXB11 transfectant pools (i.e. colonies) were step amplified to a final 250 nM MTX concentration as described by Rasmussen et al., 1998 supra.

Clonal Flt3 ligand-expressing recombinant cell lines (Veggie-CHO:FLT-3L and DXB11:FLT-3L) were isolated from these final amplified pools using the 96-well limiting dilution technique. Growth and recombinant protein expression of the cultures were monitored. The Veggie-CHO:FLT-3L cells exhibited better growth; they had a shorter doubling time and reached higher cell densities than the DXB11:FLT-3L cells. These two cell lines produced similar final titers of recombinant protein.

Because Veggie-CHO cells grew independent of exogenously added peptide growth factors, the production of insulin and IGF-1 by these cells was examined. Although it was found that Veggie-CHO cells do not upregulate endogeneous insulin or IGF-1, these cells have more IGF-1 receptors than either DXB11 CHO, or CHO cells adapted to growth in serum-free medium containing IGF-1. In the absence of IGF-1, phosphorylation of the IGF-1 receptor was not up regulated in Veggie CHO cells. However, when grown in medium lacking IGF-1, Veggie CHO cells did have an increase in basal phosphorylation of PKB. Moreover, when IGF-1 was added to the growth media, intracellular PKB became hyperphosphorylated. This increased sensitivity to IGF-1 signaling and the absence of overexpression of endogeneous IGF-1 in the cells themselves indicate that Veggie-CHO cell lines have an increase in IGF-1-signaling through PKB.

EXAMPLE 2

Cloning The PKB Gene From CHO Cells

Total RNA was purified from DXB-11 CHO cells using a RNeasy Mini Kit (Qiagen, Santa Clarita, Calif.) and was reverse transcribed into cDNA using a First Strand cDNA Synthesis Kit (Amersham Pharmacia Biotech, Piscataway, N.J.). The A allele of the protein kinase B (PKB) gene was amplified from the cDNA by polymerase chain reaction as a Not I cassette using the following oligonucleotides:
5'-TTGCGGCCGCATGAACGACGTAGCCATTGTG-3' (SEQ ID NO:1) and
5'-AATAATGCGGCCGCTCAGGCTGTGCCACTGG-3' (SEQ ID NO:2) and the Expand Hi Fidelity PCR System (Boehringer-Mannheim Biochemicals). The amplified pkb gene fragment was purified on a 6% polyacrylamide gel, and the appropriate band cut from the gel and eluted with 0.1×SSC overnight at 37° C. Following ethanol precipitation, the amplified fragment encoding the pkb A allele was cloned into pPCR-script amp SK(+) using the PCR-Script Amp Electroporation-Competent Cell Cloning Kit (Stratagene, La Jolla, Calif.). Several clones were selected and sequenced by standard methods. One of these, the A4 clone, was chosen and named pCR-pkbA4. The PKB gene was then transferred as a Not I fragment into the Not I site of plasmid pcDNA3 (Invitrogen) to create plasmid pcDNA3-PKBA. The composition of the final plasmid was verified by sequence analysis.

EXAMPLE 3

Cloning and Expression of an IL-1R Type II Gene

An IL-1 receptor, cloned from B cells by mammalian expression, is expressed in many cell types (McMahan et al, 1991, EMBO J. Vol 10: 2821–2832). A huIL1R type II cDNA fragment, which encodes the 346 amino acids comprising the extracellular domain of the IL1R type II protein including the signal sequence, was generated through PCR using IL1R type II cDNA as a template DNA. The pG3.6I-huIL1R type II vector was constructed by subcloning a Stu1-NotI fragment encoding the soluble human IL1R type II into Smal-NotI cut pG3.6I. The CHO expression vector pG3.6I is a derivative of pG3.6 (Aldrich et al., 1998, Cytotechnology 28:9–17) containing an IRES (Jang et al., 1991, Genes Dev. 4:1560–1572) sequence between the cDNA encoding the gene of interest and the cDNA encoding DHFR.

A CHO cell line expressing human IL1R type II (the 25H9 cell line) was constructed by transfecting CHO cells with the pG3.6I-huIL1R type II stable expression vector using the well-known lipofectamine transfection method. The CHO cells used for transfections were previously adapted to growth in serum-free medium containing Long$^3$-IGF-1 (commercially available from JRH Biosciences Inc., Lenexa, Kans.). The 25H9 cloned cell line was derived from the pG3.6I-huIL1R type II vector transfected pool that was selected and amplified in 300 nm methotrexate.

EXAMPLE 4

Transfer of PKB Expression Plasmid into 25H9 Cell Line

The PKB expression plasmid, pcDNA3-PKBA, and the control empty vector, pcDNA3, were separately transfected into the 25H9 cell line using lipofectamine. The transfections were done in triplicate using 10 μg of plasmid DNA complexed with 100 μl lipofectamine (Gibco BRL, Rockford, Md.) for 1×10$^7$ cells. Pools of cells were transfected with either pcDNA3-PKBA or pcDNA3 (empty vector), and the cell pools were designated PKB-F, PKB-G, PKB-H, pcDNA3-F, pcDNA3-G, and pcDNA3-H. Cells were grown in a serum-free medium containing LongR$^3$-IGF-1 and allowed to recover in a nonselective medium.

After 3 days, the cells were transferred to a selective medium containing 400 μg/ml G418 (Gibco). The cells were passaged every 2 to 3 days until they reached 90% viability. The pools were then transferred to a selective medium containing G418 without LongR$^3$-IGF-1, without peptone, or without both LongR$^3$-IGF-1 and peptone.

EXAMPLE 5

Recombinant Production of IL-1R Type II in Serum-free, Protein-free Medium From Pools of 25H9 Cells Transfected With PKB Expression Plasmid The PKB pools described in Example 4, and parental 25H9 cells (CL25H9) were passed for two days in spinner flasks. These cells were then used to seed shaker flasks at 31° C. containing serum-free medium with peptones and an osmolality of 300 mOsm. Two shake flasks were set up for each cell pool: one contained IGF-1-free medium; and the other contained medium with LongR$^3$-IGF-1. 125 ml shaker flasks were seeded with 30 mLs of cells at approximately 3.0×10$^6$ cells/mL. 1 mM of sodium butyrate was added to the culture. The shaker flasks were vented on day 0. During production phase of the IL1R type II protein, cultures were monitored by sampling for viable cell density (VCD), percent viability, pH, glucose, and lactate every other day or every third day. An amino acid feed, which raised the amino acid concentrations by 4 mM L-Glutamine, 2 mM L-Asparagine, 0.5 mM L-Isoleucine, 0.8 mM L-Leucine, 0.15 mM L-Tryptophan and 0.363 mM L-phenylalanine, was given on the fourth day.

Figure 1B:
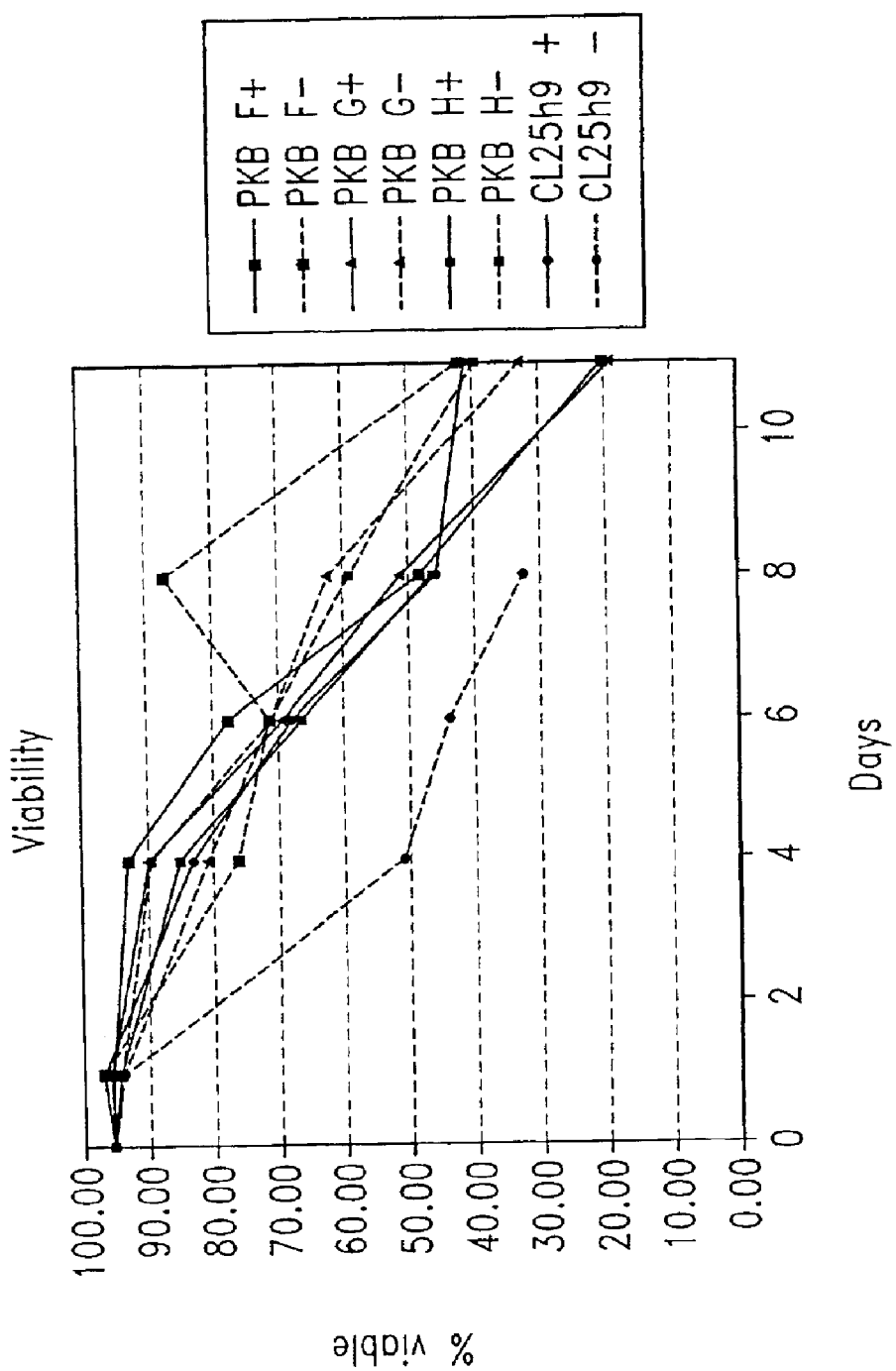

As shown in FIG. 1, PKB pools cultured without LongR$^3$-IGF-1 produced higher titers of the desired protein (FIG. 1A) and exhibited greater cell viability (FIG. 1B) than the parental cell line, CL25H9 cultured without LongR$^3$-IGF-1. For PKB pools H and F without LongR$^3$-IGF-1, the titers of the desired protein were comparable to the parental cell line cultured with LongR$^3$-IGF-1, indicating that over-expression of PKB in CHO cells allows for production runs without the necessity of adding growth factor.

EXAMPLE 6

Recombinant Production of IL-1R Type II in Serum-free, Protein-free, Peptone-free Medium From Pools of 25H9 Cells Transfected With PKB Expression Plasmid This experiment was designed to test the effect of over-expressing PKB on production of a protein of interest in serum-free medium lacking both proteins and peptones. The parental cell line 25H9 that expresses IL-1R type II (labeled CL25H9 in the figures), the PKB H pool, and one of the empty vector pools described in Example 4, which had been adapted to grow in IGF-1-free medium, were examined for expression of IL-1R type II.

Figure 2A:
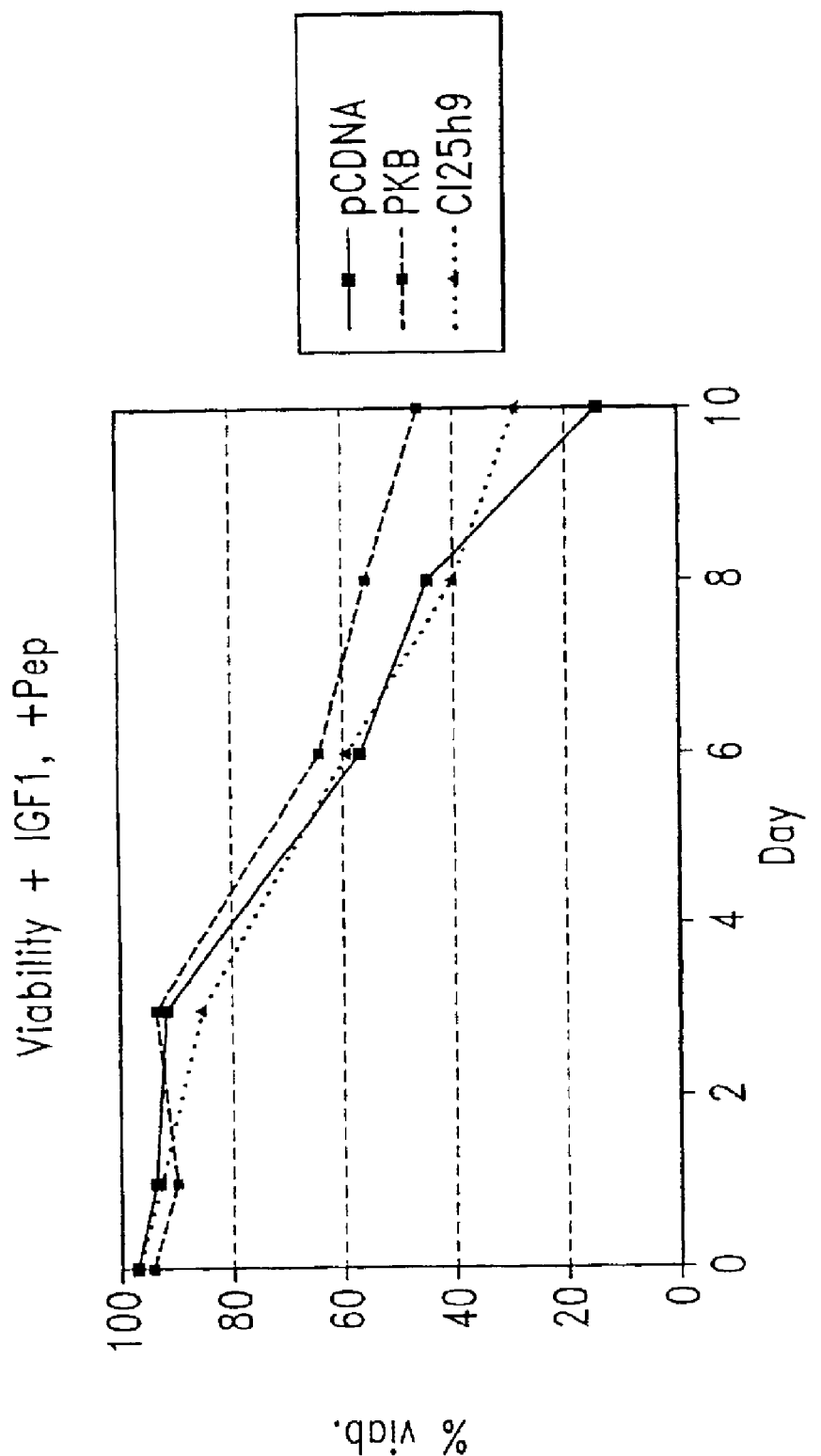
FIGS. 2A and 2B show the percentage viability and titer of the protein of interest, respectfully. The pools were tested in media with 5 g/L Hy-Soy peptones and 1 ng/mL IGF-1. C125h9 indicates the parental cells expressing the protein of interest; PKB indicates the parental cells transfected with the PKB expression plasmid; and pCDNA indicates the parental cells transfected with the empty (pcDNA3) vector.
Figure 2B:
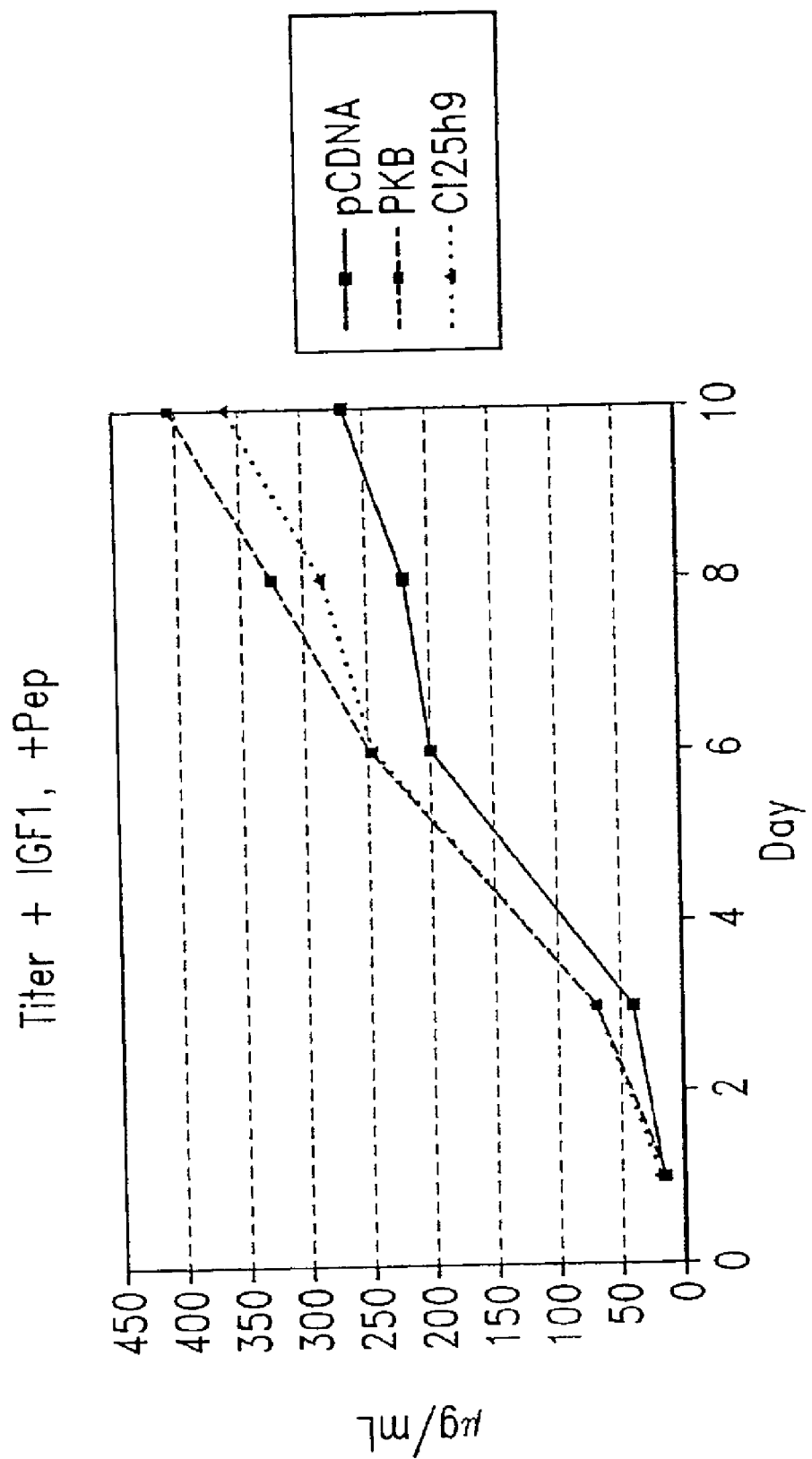
Figure 3A:
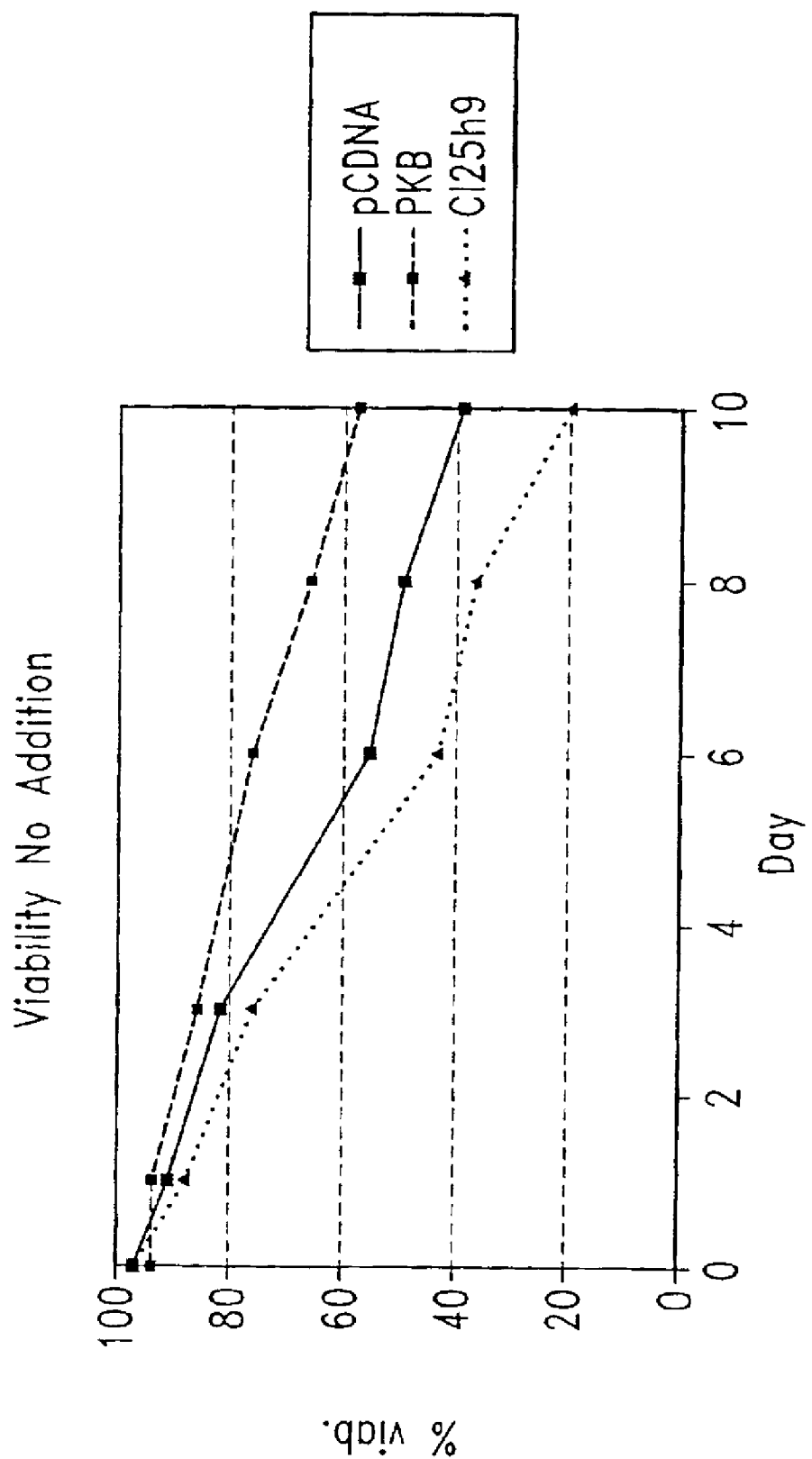
FIGS. 3A and 3B show the percentage viability and titer of the protein of interest, respectfully. The pools were tested in media without Hy-Soy peptones and without IGF-1. C125h9 indicates the parental cells expressing the protein of interest; PKB indicates the parental cells transfected with the PKB expression plasmid; and pCDNA indicates the parental cells transfected with the empty (pcDNA3) vector.
Figure 3B:
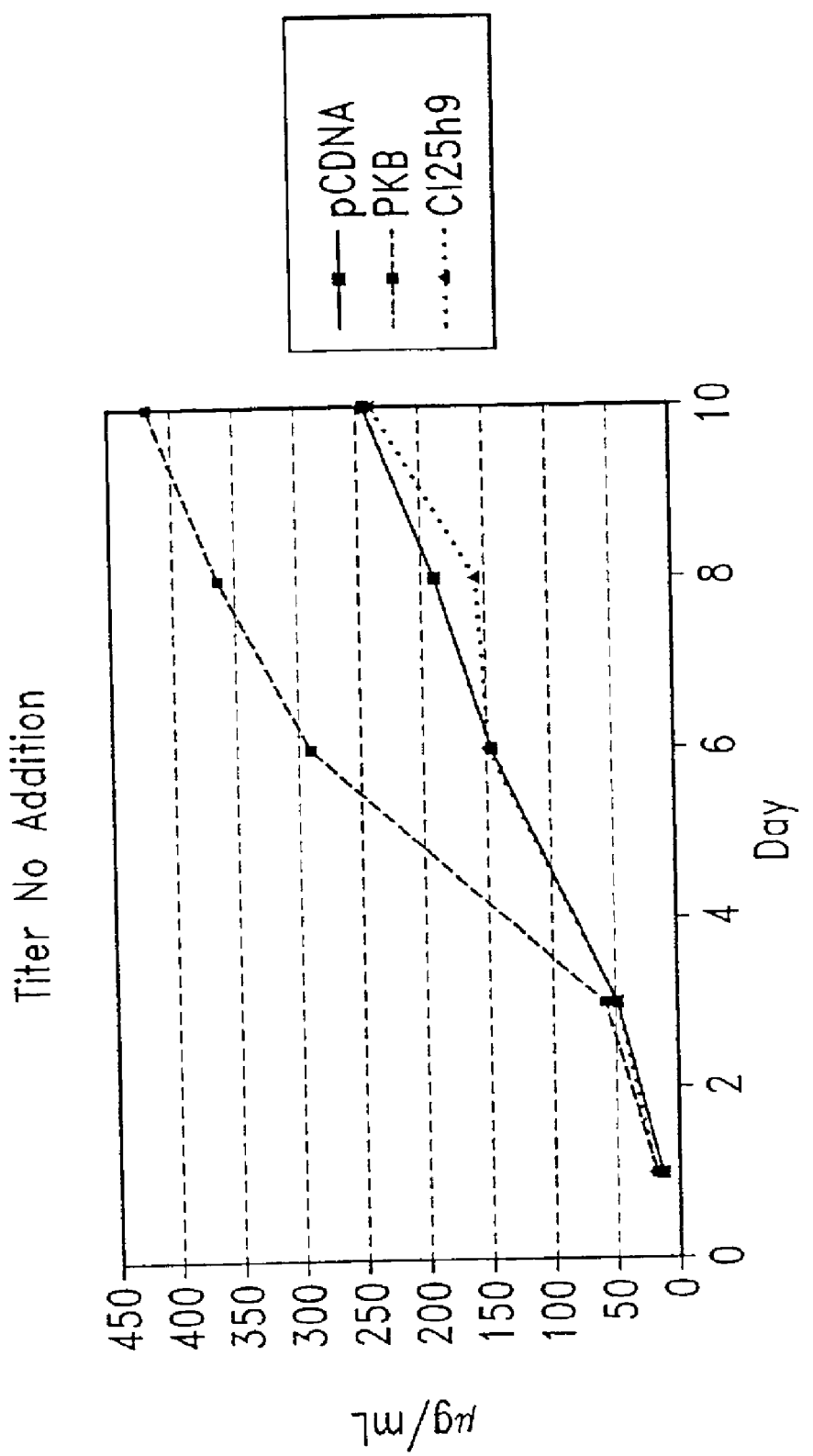

The amino acid feed disclosed in Example 5 was given on day 4. The cell lines were grown in either (1) production medium that contained peptone and LongR$^3$-IGF-1 (FIGS. 2A and B), or (2) production media did not contain peptone and IGF-1 (FIGS. 3A and B). As shown in FIG. 3A, cells expressing PKB maintained a higher viability than the parental cells or a cell pool transfected with pcDNA3 control plasmid. On day 10 of the culture, the PKB pool had significantly higher viability compared with the parental cells, C125H9, or the pcDNA empty vector pool. In FIG. 3B, it can be seen that the PKB pool had significantly higher titers than the parental cells, C125H9, or the pcDNA empty vector pool. FIGS. 2A and B demonstrate that even when the production cultures are set up in medium containing LongR³-IGF-1 and peptones, the PKB pool exhibited better viability and somewhat higher production of the protein of interest.

EXAMPLE 7

Western Blot Analysis of MAPK

This study examined the expression and phosphorylation of MAPK in Veggie-CHO cells (which grow in serum-free medium and are growth factor-independent) and in CHO cells which grow in serum-free medium and but require peptide growth factor in stock (growth) cultures and in response to removal of IGF-1, or addition of IGF-1.

In order to determine the effects on MAPK of removing IGF-1, the Veggie-CHO cell line, which is adapted to growth in serum-free, protein-free (and IGF-1 free) medium, and a cell line adapted for growth in just serum-free medium were each cultured at a cell density of 2×10⁶cells/ml in serum-free medium with LongR³-IGF-1 at a final concentration of 100 ng/ml. Cells were then switched to serum-free medium with out any IGF-1, and 5×10⁶ cells of each cell type were harvested at various times after culture (i.e., 0.5 hr, 1 hr, 4 hr, 8 hr).

In order to determine the effects on MAPK of adding IGF-1, the Veggie-CHO cell line, which is adapted to growth in serum-free, protein-free (and IGF-1 free) medium, and a cell line adapted for growth in just serum-free medium were each cultured for 8 hours at a cell density of 2×10⁶ cells/ml without IGF-1 in a serum-free, protein-free growth medium. LongR³-IGF-1 was then added to a final concentration of 100 ng/ml. 5×10⁶ cells of each cell type were harvested at various times after LongR³-IGF-1 additions (i.e., 5 minutes, 0.5 hr, 1 hr, 4 hr, 8 hr).

Cells from the above described experimental samples, along with CHO stock cultures adapted to growth in serum-free, protein-free medium, and CHO stock cultures adapted to growth in serum-free medium (which had been maintained with 100 ng/ml LongR³-IGF-1) were harvested and Triton detergent solubilized. The resulting cell extracts were analyzed on 2×SDS-PAGE 4%–20% Tris Glycine gels and electroblotted onto nitrocellulose. Western blots were probed with anti-phospho MAPK antibody (Promega Corporation, Madison, Wis.) to detect only the phosphorylated form of MAPK in the extracts.

Figure 4:
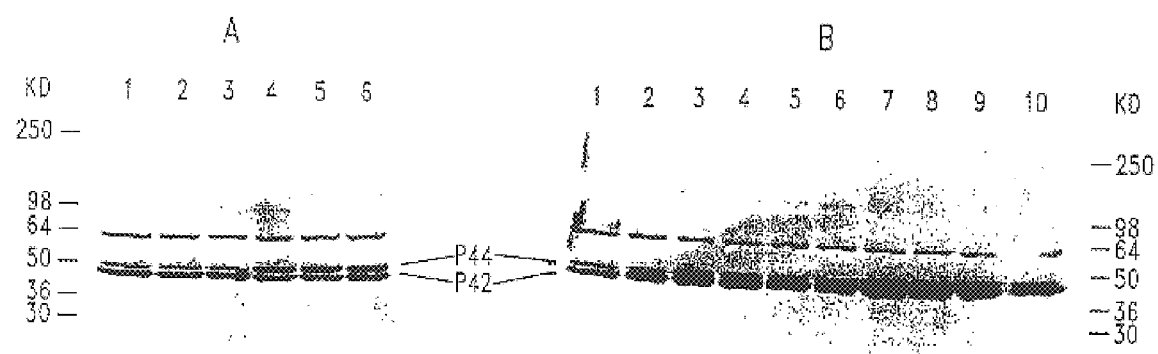
FIG. 4. Analysis of MAPK expression and phosphorylation in extracts from CHO cells grown in serum-free, protein-free medium and in extracts from CHO cells grown in serum-free medium in response to IGF-1. Both Panel A and Panel B are Western blots that were probed with anti-phospho MAPK antibody to detect only the phosphorylated form of MAPK in the cell extracts. Panel A presents the results from a time course experiment in which cells were transferred from medium containing LongR$^3$-IGF-1 to IGF-1-free medium. Lanes 1 to 3 are extracts from CHO cells cultured in serum-free medium with Long$^3$-IGF-1 (lane 1), or initially grown with LongR$^3$-IGF-1 and then switched to IGF-1-free medium for 30 minutes (lane 2) or 4 hours (lane 3). Lanes 4 to 6 contain extracts from Veggie CHO-cells grown without IGF-1 at 0 minutes (lane 4), 30 minutes (lane 5) or 4 hours (lane 6) after the start of the experiment. Panel B shows the results from an experiment in which LongR$^3$-IGF-1 is again added to the medium after 8 hours of culture in IGF-1-free medium. Lane 1 in Panel B contains extracts of CHO cells cultured in serum-free medium without IGF-1 for 8 hours. Lanes 2 to 5 contain cell extracts harvested at 5 minutes (lane 2), 30 minutes (lane 3), 1 hour (lane 4), or 4 hours (lane 5) after LongR$^3$-IGF-1 re-addition. Lanes 6 to 10 contain Veggie-CHO cell extracts harvested before IGF-1 addition (lane 6), 5 minutes (lane 7), 30 minutes (lane 8), 1 hour (lane 9) or 4 hours (lane 10) after LongR$^3$-IGF-1 addition.

As FIG. 4 shows, the basal level of MAPK phosphorylation observed in the CHO cells adapted to growth in serum-free, IGF-1-free medium is higher than that detected in the CHO cells adapted to growth in serum-free medium with or without the addition of LongR³-IGF-1. The larger size signal of the MAPK doublet (containing MAPK p44 and MAPK p42) was significantly more intense in samples grown in serum-free, protein-free medium than in samples grown in serum-free medium, both with the anti-phospho MAPK and the anti-MAPK antibodies, suggesting that expression and phosphorylation of MAPK is upregulated in CHO cells adapted to growth in serum-free, protein-free medium. Both in the absence of IGF-1 and upon addition of IGF-1, ERK2/MAPK p44 and to a lesser extent ERK1/MAPK p42 were more highly phosphorylated in the Veggie-CHO cultures than in the CHO cells adapted to growth in serum-free medium. This increase in phosphorylation could be a result of the observed increased MAPK kinase (MEK) activity, or due to decreased MAPK phosphatase activity in Veggie-CHO cells.

EXAMPLE 8

Cloning Of CHO MEK Gene

Wild type CHO MEK genes were amplified from CHO cell cDNA in two PCR reactions. The primer set used for the first amplification was 5'-GGATCCGCCGCCACCATGCCCAAGAAGAAGC CGAC-3' (SEQ ID NO:3) with 5'-CTGGAGTCTCTCGGGCGACATGTAT-3' (SEQ ID NO:4). The second PCR amplification used primers 5'-CCCGAGAGACTCCAGGGGACT-3' (SEQ ID NO:5) with 5'-GCGGCCGCTCAGATGCTAGCGGCATGGGTT-3' (SEQ ID NO:6). The MEK PCR fragments were sized on 6% polyacrylamide gels and cut from the gels and eluted with 0.1×SSC overnight at 37° C. Following ethanol precipitation, the fragments were each cloned into plasmid pPCR-script Amp SK(+) (Stratagene, La Jolla, Calif.). The MEK gene fragments were verified by sequence analysis and then cloned into plasmid pCDNA3 in a three way ligation. The resulting plasmid was called pwtMEK-1.

The MEK gene was transferred from plasmid pwtMEK-1 to plasmid pcDNA3.1/Zeo+ (Invitrogen, Carlsbad, Calif.) as a BamHI-NotI fragment. This plasmid was named pwtMEK-20 and was sequenced to confirm the presence of the MEK gene.

EXAMPLE 9

Construction of Plasmids and Cell Lines

Construction of a Recombinant Cell Line Expressing Human TNFR:Fc

The molecular cloning of DNA encoding the human 75-80 kDa tumor necrosis factor receptor (TNFR) has been described in detail in U.S. Pat. No. 5,395,760 and Smith et al., 1990, Science 248:1019, 1990. TNFR:Fc is a fusion polypeptide comprising an extracellular domain of TNFR linked to a constant region from human IgG. The primary translation product is a single molecule of soluble TNFR linked to a single chain of Fc derived from human IgG1. Following translation, but prior to secretion, this fusion molecule dimerizes via cysteine residues in the Fc region. TNFR: Fc fusion polypeptides have been described in, inter alia, U.S. Pat. No. 5,605,690.

The construction of the TNFR:Fc mammalian expression vector pCAVDHFRrhuTNFR:Fc, is described in U.S. Pat. No. 5,605,690. The pCAVDHFRrhuTNFR:Fc vector was transfected into DXB-11 CHO cells using Lipofectin™ reagent from Gibco BRL. Approximately 10 µg of DNA was added to 10 tissue culture plates containing 2×10⁶ DXB-11 CHO cells. After transfection, cells were selected for the expression of DHFR, and the resulting colonies were transferred to 24-well plates and analyzed for TNFR:Fc expression. For amplification, the highest expressing cultures were exposed to increasing concentrations of methotrexate, and cells able to grow at 25 nM methotrexate were cloned by limiting dilution into 96-well plates. The highest expressing clones were transferred to suspension culture. The cell line "2A5-3" was chosen for further work, based upon its high level of TNFR:Fc expression.

Construction of PKB Plasmid

The A allele of the CHO protein kinase B (pkb) gene was cloned into an expression vector as described above in Example 2.

Construction of Myristylated PKB Plasmid

A myristylated deletion mutant of the CHO PKB gene was constructed. This myrPKB mutant was made because it was expected to be more active than wild-type PKB by virtue of its localization to the cell membrane. A DNA fragment encoding the gene was amplified by PCR from the pCR-pkbA4 described above in Example 2. The primers used were 5-CCCGGGCCGCCACCATGGGGAGTAGCAAGAGC AAGCCTAAGGACCCCAGCCAGC GCAACGACGGGGCTGAGGAGATGGAGGTGT-3' (SEQ ID NO:7) and 5'-AATAATGCGGCCGCTCAGGCTGTGCCACTGG-3' (SEQ ID NO:8). The first primer above added a SmaI restriction site, a Kozak sequence and the src myristylation signal (Cross et al., 1984, Mol. Cell. Biol. 4:1834–1842). It also deleted amino acids 4–129 of the pkb gene (Kohn et al., 1996, J. Biol. Chem. 271:21920–21926). The PCR were performed using the Expand Hi Fidelity PCR System (Boehringer-Mannheim Biochemicals).

The myristylated pkb gene fragment was purified from a 6% polyacrylamide gel. It was cut from the gel and eluted with 0.1×SSC overnight at 37° C. Following ethanol precipitation, the fragments were each cloned into plasmid pPCR-script Amp SK(+) (Stratagene, La Jolla, Calif.). The myristylated pkb gene was sequenced from four clones. One of the clones with the correct sequence was selected and named pCR-mpkbA3. The myristylated pkb gene from this plasmid was cloned into pcDNA3 as a SmaI-NotI fragment. This plasmid was named pcDNA3-mpkbA3.

EXAMPLE 10

Transfection of Cell Lines With MEK Expression Plasmid

Using 2–3 day old cells, 10 cm tissue-culture dishes were seeded with 2.5×10$^6$ cells/ml/dish in fresh adherent growth media and then incubated at 37° C., 5% $CO_2$. For each of three cell lines, 2A5-3, 2A5-3 supertransfected with pcDNA3-pkbA and 2A5-3 supertransfected with pcDNA3-mpkbA3, five dishes were seeded. For each dish to be transfected, 15 μg of DNA (pwtMEK1 or pwtMEK20 from Example 8) was diluted into 0.8 ml of a serum-free transfection medium containing Hepes, GHT, DMEM F-12, L-Gln and LongR$^3$-IGF-1 in a tube. A lipofectamine (GibcoBRL) mixture sufficient for 200 μl lipofectamine/dish in 0.8 ml/dish total was made in the serum-free transfection media. To each DNA sample, 800 μl Lipofectamine/SFTM mix was added for a total of 1.6 ml per dish, mixed gently and incubated at room temperature for 30 minutes.

When the confluency of the dishes was approximately 60%, each dish was rinsed twice with the serum-free transfection media and 6.4 ml of the transfection media was added to the DNA/lipofectamine mixture, mixed gently and deposited on the cells. The dishes were then incubated at 37° C. in 5% $CO_2$ for 6 hours. The transfection mix was then aspirated and discarded and the dishes refed with 10 ml of an appropriate growth medium and replaced in the incubator.

After 3–5 days post-transfection, the cells were removed by trypsinization and counted via trypan-blue exclusion on a hemocytometer. The cells were then seeded into T175 flasks at approximately 2.5–4.0×10$^6$ cells/30 ml/flask. To the 2A5-3/PKB/MEK and 2A5-3/myrPKB/MEK cells, the selective agent Bleocin™ was added to the growth media at 30 μg/ml to select for the plasmid containing the MEK gene. The flasks were then with media containing 200 μg/ml of Zeocin™ as the selective agent. The dosage of Zeocin™ was reduced to 50 μg/ml after stable cultures were obtained. 400 μg/ml of G418 (Neomycin) was added to the 2A5-3/MEK transfected cells as the selective agent and the dosage was reduced to 200 μg/ml after stable cultures were obtained.

After approximately 10 days of selection, the cells formed confluent monolayers in their respective flasks. The cells were then placed in reduced drug media as described above and the cultures expanded. The cells from each transfection pool were then seeded into shake-flasks for suspension adaptation.

EXAMPLE 11

Adaptation of Adherent Transfected Pools to Suspension Growth

Two pools from each of the transfections of Example 10 were adapted to suspension growth. Cells were seeded in 30 ml at 4×10$^5$ cells/ml in a suspension media in 125 ml shake-flasks and cultured at 37° C. at 160 rpm. These cells were subcultivated by centrifugation every 2–3 days to 4–5×10$^5$ cells/ml. After one week, the cells had successfully adapted to suspension growth as demonstrated by the sustained viabilities and reasonable growth shown in FIG. 6.

EXAMPLE 12

Western Blot Analysis of MEK Expression in MEK Transfectant Pools

Figure 5A:
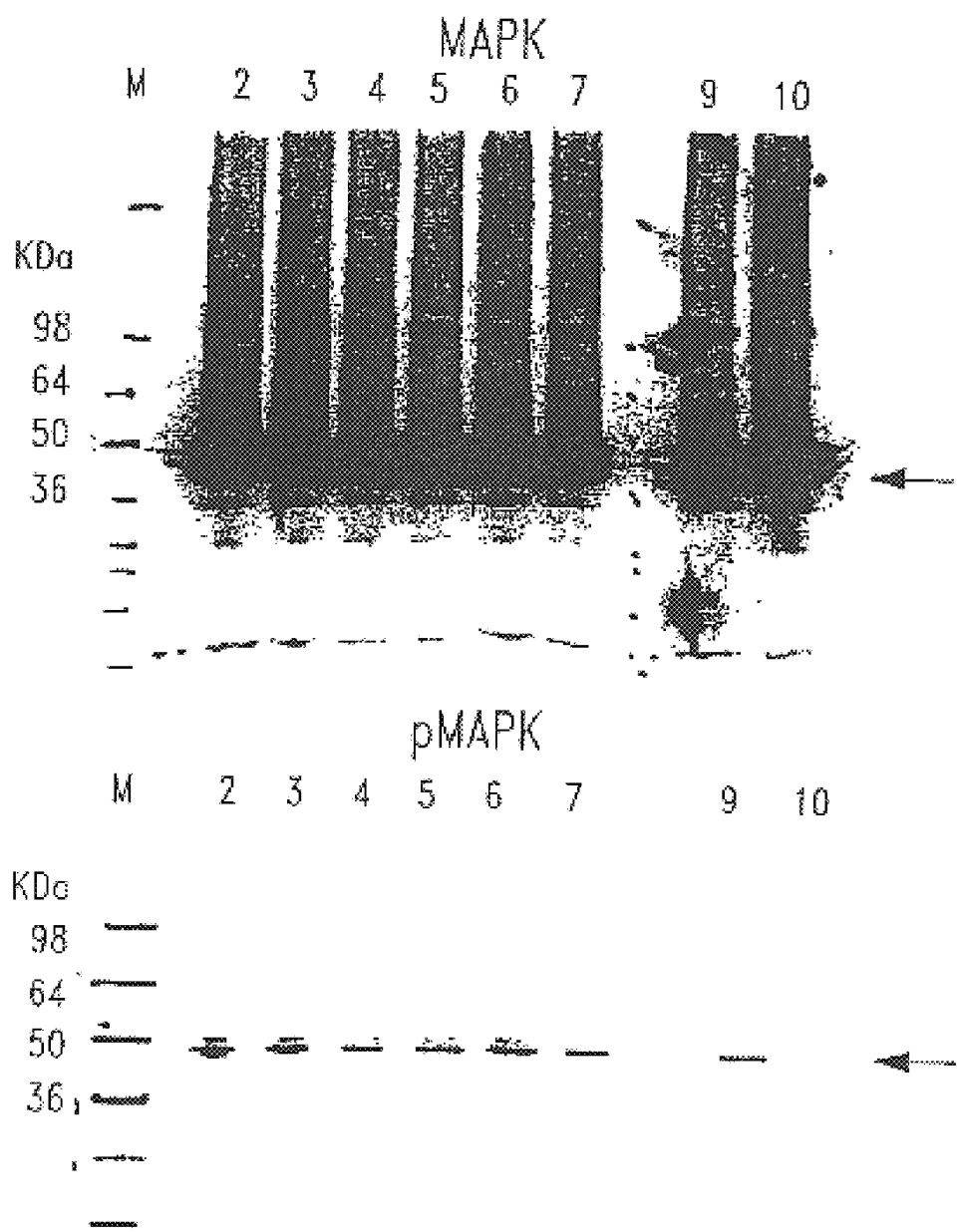
FIG. 5A demonstrates the total MAPK protein present in the cell extract or total phosphorylated form of MAPK in the cell extract.

The suspension-adapted MEK transfectant pools of Example 11 were analyzed on western blots to examine MEK expression and MAPK expression and phosphorylation in these cells. Cells (5×10$^6$) were resuspended in 250 μl Triton cell lysis buffer and incubated on ice 15 minutes. These cells were then centrifuged at approximately 13,000 rpm for 15 minutes at 4° C. The clarified detergent solubilized cell extracts were analyzed by western blot analysis. The extracts were electrophoresed on 4–20% Tris-glycine SDS-Page gels and electroblotted into nitrocellulose. Blots were probed with anti-MAP antibody (MAPK; Santa Cruz Biotechnology, Santa Cruz, Calif.) to detect total MAPK protein present in the cell extracts or probed with anti-phospho-MAPK (Promega Corp., Madison, Wis.) to detect only the phosphorylated form of MAPK in the cell extracts (FIG. 5A). A second set of blots containing the sample cell extracts were probed for MEK and phospho-MEK using antibodies from New England Biolabs Inc. (Beverly, Mass.).

Figure 5B:
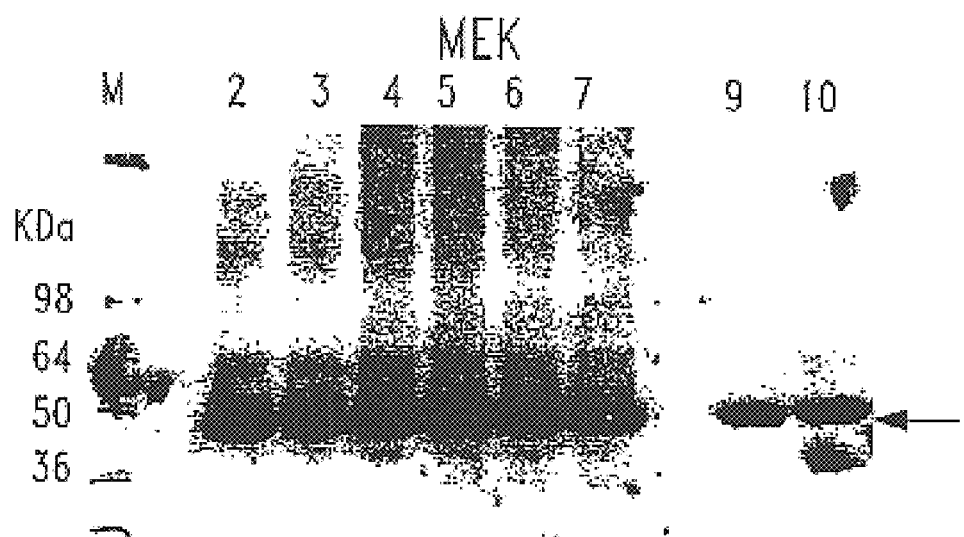
FIG. 5B shows a Western blot demonstrating the total MEK protein present in the cell extracts and total phosphorylated form of MEK in the cell extract. M=molecular weight markers; lanes 2 and 3: 2A5-3/MEK pools 1 and 2 respectively; lanes 4 and 5: 2A5-3/PKB/MEK pools 1 and 2 respectively; lanes 6 and 7: 2A5-3/myrPKB/MEK pools 1 and 2, respectively; lane 9: 2A5-3/pcDNA3 (empty vector control); lane 10:IL 1R Type II Clone 25H9/PKB (for comparison).
Figure 5B:
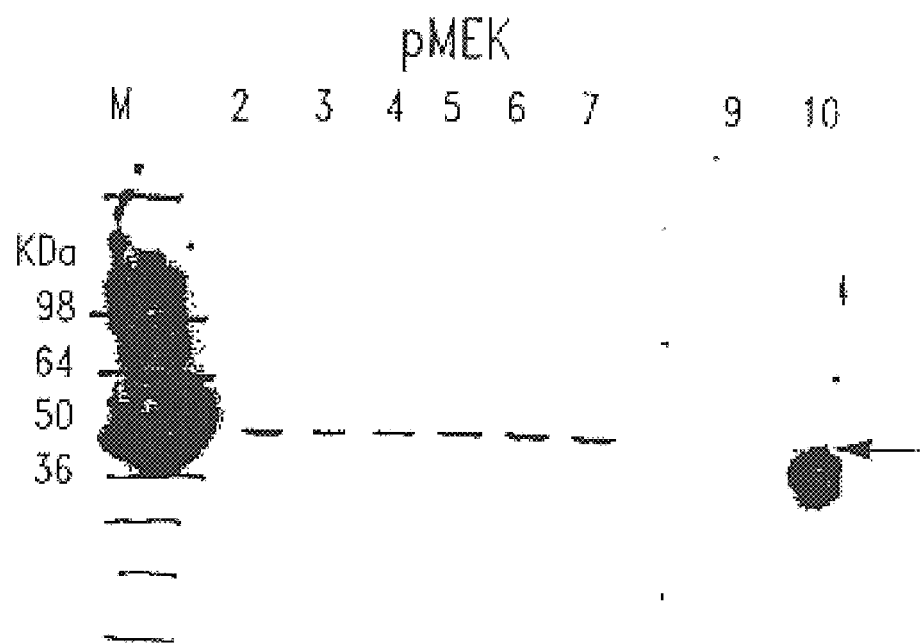

The results are shown in FIG. 5. Lanes are as follows: M=molecular weight markers; lanes 2 and 3:2A5-3/MEK pools 1 and 2 respectively; lanes 4 and 5: 2A5-3/PKB/MEK pools 1 and 2 respectively; lanes 6 and 7: 2A5-3/myrPKB/MEK pools 1 and 2, respectively; lane 9: 2A5-3/pCDNA3; lane 10: IL1R Type II Clone 25H9/PKB. The arrow indicates the position of MAPK (FIG. 5A) or MEK (FIG. 5B). These results demonstrate that the MEK protein was overexpressed and that the substrates for MEK (MAPK p44 and p42) were hyperphosphorylated in the MEK-transfected cell pools.

EXAMPLE 13

Figure 6:
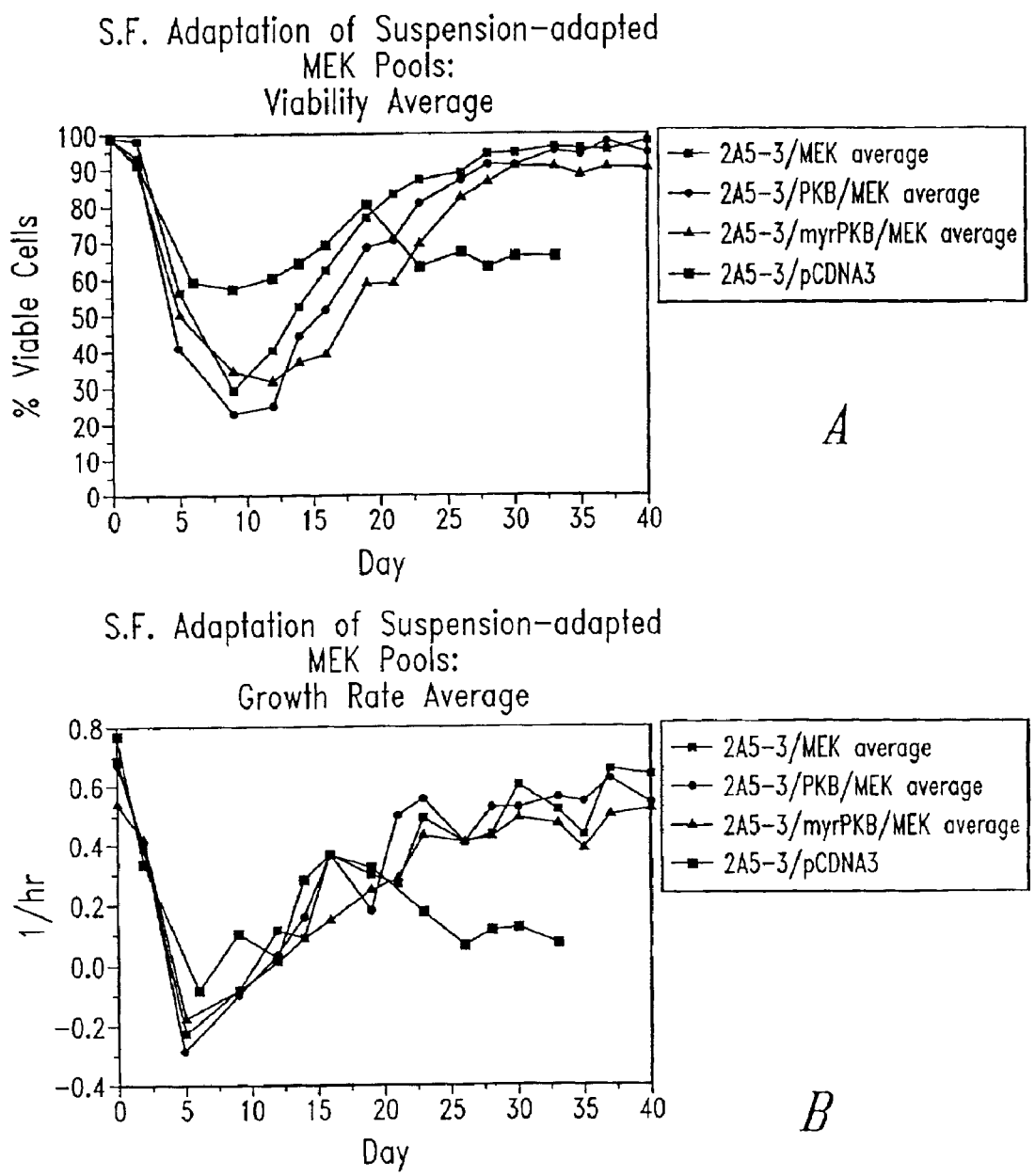
FIG. 6. Suspension-adapted pools in serum-containing media were seeded into serum-free suspension media at seeding densities of 6×10$^5$ cells/ml and cultured at 160 rpm at 37° C.

Serum-Free Adaptation of MEK1-Transfected, and MEK1/PKB-Transfected Cell Pools Each of the suspension-adapted pools of Example 11 was seeded into shake-flasks at 6×10$^5$ cells/ml and subcultivated every 2–3 days in serum-free medium containing LongR$^3$-IGF-1 and peptones. When the growth rate of the cultures began to recover to levels of serum-containing pools, the initial seeding density was gradually lowered to 4×10$^5$ cells/ml. As seen in FIG. 6, cells began to recover after 10 days in the serum-free medium. Consistently high viabilities and good growth were attained after subcultivation of the MEK transfected pools in serum-free medium for three weeks. With the exception of 2A5-3/pcDNA3, the cultures recovered and attained cell viability above 90% and growth rates of approximately 0.75 generation/day.

These results demonstrate that overexpression of MEK in DXB-11 cells facilitates their rapid and direct adaptation to serum-free growth. The overexpression of PKB along with MEK does not appear to enhance the serum-free adaptation process. However, overexpression of PKB could aid in adaptation to other culture conditions (e.g., absence of growth factor or peptones).

EXAMPLE 14

IGF-1 and/or Peptone Elimination From MEK1-Transfected, and MEK1/PKB-Transfected Cell Pools Adapted to Serum-Free Growth The serum-free adapted pools from Example 13 were then evaluated for their ability to survive in either IGF-1-free or peptone-free media. As before, each of the pools were seeded in shake-flasks at 6×10$^5$ cells/ml and subcultivated every 2–3 days. As the cells recovered and adapted to the leaner medium, the seeding density was lowered as discussed above. Results from this experiment are summarized in the following table.

TABLE 1

Summary of results for IGF-1 or Peptone removal experiment with serum-free-adapted 2A5-3/MEK pools.

| Condition | 2A5-3/ pCDNA3 | 2A5-3/MEK | | 2A5-3/ PKB/MEK | |
|---|---|---|---|---|---|
| | | Pool 1 | Pool 2 | Pool 1 | Pool 2 |
| +Serum Stock | | | | | |
| Days in expt. | 31 | 47 | 47 | 48 | 48 |
| Generations | 29.3 | 47.0 | 46.7 | 46.9 | 47.2 |
| Generations/day | 0.95 | 1.0 | 0.99 | 0.98 | 0.98 |
| Final viability | | 99 | 100 | 100 | 100 |
| Serum-free Stock | | | | | |
| Days in expt. | ND | 101 | 101 | 101 | 101 |
| Generations | | 69.9 | 81.1 | 77.4 | 56.4 |
| Generations/day | | 0.70 | 0.80 | 0.77 | 0.56 |
| Final viability | | 95 | 97 | 94 | 94 |
| −IGF-1 | | | | | |
| Days in expt. | ND | 18 | 56 | 18 | 56 |
| Generations | | 2.7 | 32.5 | 2.5 | 25.9 |
| Generations/day | | 0.15 | 0.58 | 0.14 | 0.46 |
| Final viability | | 59 | 99 | 47 | 98 |
| −Peptone | | | | | |
| Days in expt. | ND | 56 | 56 | 56 | 56 |
| Generations | | 44.8 | 42.4 | 48.5 | 27.7 |
| Generations/day | | 0.80 | 0.88 | 0.86 | 0.49 |
| Final viability | | 97 | 94 | 94 | 93 |

Over expression of a MEK1 gene, with or without overexpression of a PKB gene, facilitated the adaptation to growth in peptone-free media. Two of the four serum-free-adapted MEK pools survived in medium without IGF-1: one pool overexpressing MEK; and one pool overexpressing both PKB and MEK. However, more detailed analysis of the pools indicated that the PKB pool which did not adapt well to growth in medium without IGF-1 did not, in fact, express as high levels of PKB as the pool that did adapt well (as measured by Western blot). Staining of cell pools indicated that only about 10 to 15% of this pool expressed PKB (as opposed to over 90% of the pool that adapted well). Thus, PKB does appear to facilitate adaptation to growth in medium without IGF-1.

Although MEK1 overexpression facilitated rapid adaptation and growth in serum-free and peptone-free media, MEK1 expression did not consistently abrogate IGF-1 requirements. Thus, it appears that expression of PKBα, which abrogates IGF-1 requirements, could be advantageously combined with expression of MEK1. In other words, overexpression of MEK in these CHO cells appears to facilitate growth in serum-free and/or peptone-free media, and overexpression of PKB appears to facilitate growth factor independent growth (specifically, protein growth factors).

EXAMPLE 15

Transfection of CHO Cells With Glut5 Expression Vector

The human glucose transporter 5 (Glut5) encoding sequence was cloned using RT-PCR. Human small intestinal cDNA was purchased from Clonetech (Palo Alto, Calif.) and used in PCR reaction. The primers 5'-CCACCATCTAGATCACTGTTCCGAAGTGACAG GT-3' (SEQ ID NO:9) and 5'-CCCCAAGCTTGTCGACGCCGCCACCATGGAGC AACAGGATCAGAGCATGAA-3' (SEQ ID NO:10) were used in the PCR reaction. The PCR product was subsequently cloned into the EcoRV-NotI sites of pCDNA3 for expression in CHO cells.

Cells growing in serum-free medium were transfected in triplicate with pcDNA3-glut5 and pcDNA3 using lipofectamine. For selection, the cells were seeded at 6×10$^5$ c/ml into medium containing glucose, HySoy peptones, L-gln, LongR$^3$-IGF-1, Intralipids and G418. Seeding density was 8×10$^5$ c/ml for passages 1 and 2 and then returned to 6×10$^5$ c/ml.

Upon reaching ≧90% viability, the pcDNA3-glut5 and pcDNA3 pools were placed in a selection medium containing sodium bicarbonate, ferrous sulfate, pluronic F-68, LongR$^3$-IGF-1, Hepes, sodium chloride and fructose. This medium did not contain glucose and was called fructose selective media. The pools were seeded at a density of 8×10$^5$ cells/ml. Though the pcDNA pools died within one passage, the glut5 pools (glut5-B, glut5-C and glut5-D) were carried for 12 to 35 passages in the medium.

Figure 7:
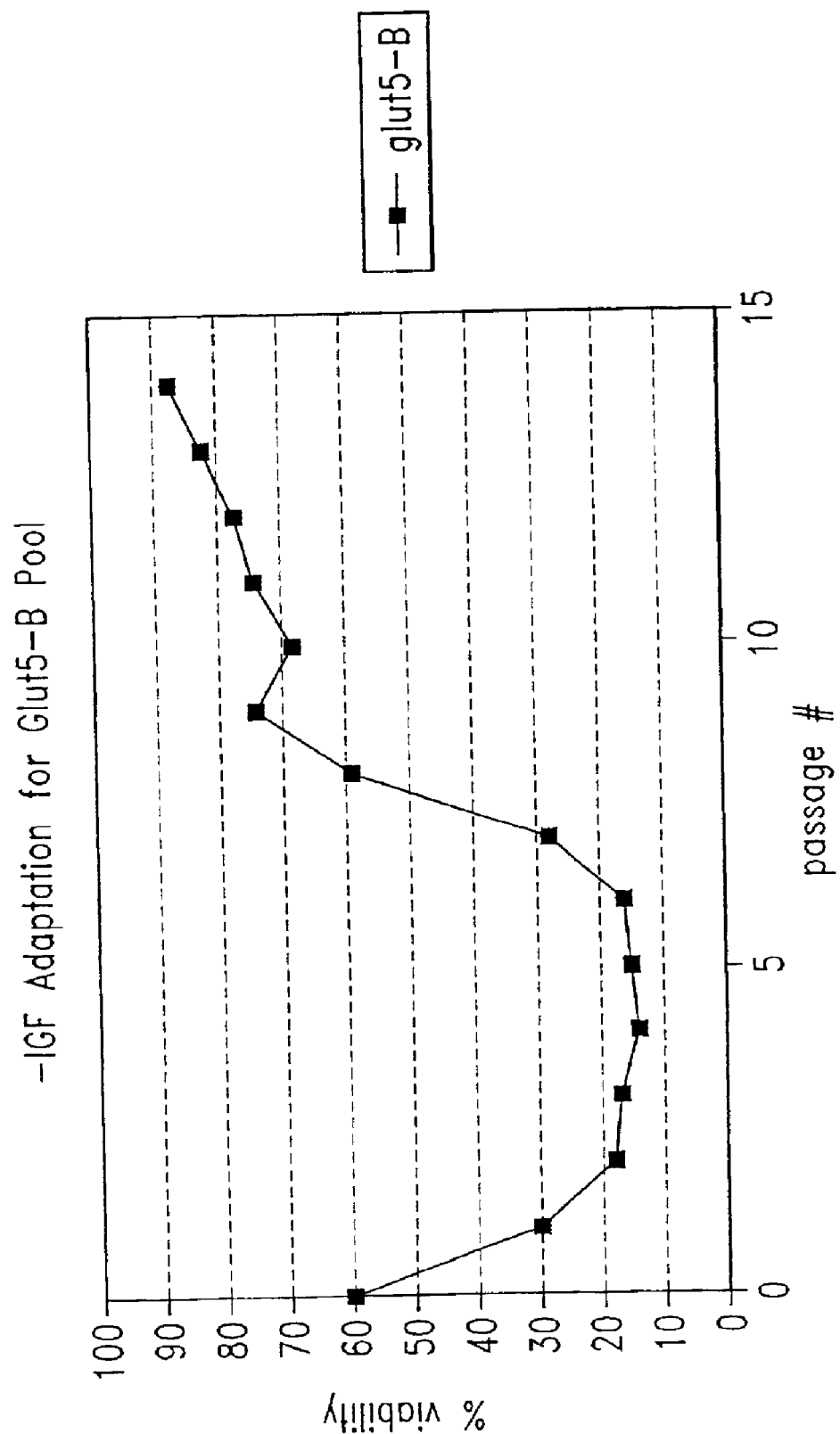
FIG. 7. Adaptation of Glut5-B pool to growth in IGF-1-free medium.

Glut5-B pool was selected and seeded in the glucose-free selection medium described above without LongR$^3$-IGF-1 but containing fructose. Cells were passaged for 14 passages and then frozen. As shown in FIG. 7, once the glut5-B cells adapted to the selection medium without LongR$^3$-IGF-1, the viability increased to 87%.

One of the pcDNA3 transfected pools from Example 14 was thawed from −70° C. into a selection media made with glucose. Cells were passed with 60 mls volume in a 250 ml shaker flask at 37° C. three times a week by complete media exchange. Initial seeding density was 8×10$^5$ cells/ml. Cells were then passed into growth medium identical to the fructose selective media but containing glucose and not fructose until the growth rate stabilized and viability reached above 90%. The cells were then transferred into the same selection media made without IGF-1. Two attempts were made to achieve growth in this media. In both cases, the cells transfected with only the pcDNA3 vector (controls) died.

Thus, these results demonstrate that constitutive expression of glut5 overrides the need for growth factor IGF-1, and allows growth on medium containing fructose instead of glucose as an energy source.

EXAMPLE 16

Serum-free Adaption and Recombinant Protein Expression of Cells Overexpressing MEK Proteins This experiment was designed to evaluate the effect of overexpressing wild-type and mutant MEK proteins on the serum-dependence and growth-factor dependence of cell cultures. Expression vectors coding for two mutated hyperactive forms of the MEK protein (Mansour et al., 1994, Science 265:966–970) were constructed in pCDNA3. SS-mutMEK has two amino acid changes: glu in place of ser at position 218 and asp in place of ser at position 222. The Δ-mutMEK construct has the above two amino acid changes as well as a deletion of amino acids 32–51.

The two mutant MEK constructs were transfected into the 2A5-3 adherent, serum-dependent cells and the transfectants were selected and adapted to growth in suspension cultures. Three serum-free pools were set up from each of the two mutMEK-transfected suspension pools and from the 2A5-3/pwtMEK cells described in Example 10. Each pool was seeded in shake-flasks at $6 \times 10^5$ cells/ml and subcultivated every 2–3 days. After about four weeks, the 3-day passages were seeded at a lowered initial cell density of $5 \times 10^5$ cells/ml. In addition after adaptation of the cells to serum-free growth, the cells were then evaluated for growth in peptone-free, serum-free media and IGF-1-free, serum-free media.

The growth of each of the different transfectants was evaluated: the control empty vector pCDNA3 transfected cells, the wild-type MEK transfected cells and the mutant MEK transfected cells in serum-free media. Pools from all three different MEK tranfected cells grew better in serum-free media and in serum-free, peptone-free media than the control vector transfected cells. The SS-mutMEK transfected pools had the highest growth rates and best viabilities in serum-free media and in peptone-free media. The cells expressing the SS-mutMEK construct more efficiently and rapidly adaptated to serum-free growth than cells expressing the wtMEK or delta MEK constructs.

Production of recombinant protein in serum-free medium was also examined in pools of cells transfected with the pCDNA3 (empty vector), PKB/MEK, MEK, or mutant MEK expression vectors. Cells were induced in triplicate in the various media. The 2A5-3 cells transfected with the SS-Mut MEK construct consistently outperformed all other pools with respect to viability and titer. These cells maintained their initial seeding density for the entire experiment, which, in combination with higher titers, yielded the highest cumulative specific productivity. However, all of the MEK expressing constructs produced higher cumulative productivity under serum-free conditions.

Then, the performance of pCDNA3, MEK, mutant MEK transfected cells in peptone-free, serum-free production conditions was examined. Cells were induced in triplicate in serum-free media with and without peptones. Again, the MEK and mutant MEK transfected cell pools showed higher specific productivity than the control pools. In addition, the SS-Mut MEK construct consistently outperformed all other pools with respect to viability and titer.

EXAMPLE 17

Expression of PKB in COS1 and CV1 Cells

The effect of overexpressing PKB was examined in 293, COS1 and CV1 cells. The three different host cells were transformed with either pcDNA(empty vector) or pcDNA-PKB described in Examples 2 and 9. In addition, 293 and CV1 were also transformed with the pcDNA-myrPKB expression vector as described in Example 9.

The transiently transformed 293, CV1 and COS1 cell lines were supertransfected with different expression plasmids that directed expression of a recombinant protein of interest used as a reporter gene. Production of the recombinant protein in the supertransfected cells was improved in the cells overexpressing PKBα.

Similar experiments were performed with stable transformants of COS1 and CV1 cells that had been transformed with pcDNA(empty vector) or the PKB expression constructs, and then transiently supertransfected with an expression vector for a reombinant protein. Consistent increases in recombinant protein expression were not observed when examining non-clonal cell lines. However, one CV1 clone, KD4, which expresses PKB approximately 3× over background, did demonstrate improved recombinant protein expression when compared to a pcDNA clone (PF1) or another PKB clone (KD12) that expresses very little PKB protein (as measured by Western blot). Thus, increased transient recombinant protein expression appears to correlate with the level of overexpression of PKBα.

Adaptation to growth in serum-free medium was examined in the COS1 cell transformants. Results indicated that overexpression of PKB allowed COS1 cells to be cultured under serurn-free conditions.

EXAMPLE 18

Adaptation Of CV1 And 293 Cells To Culture In Serum-free Medium

CV1 cells and 293 cells stably transformed with the PKB expression vector are cultured in serum-free medium. Cells that overexpress PKB can grow in serum-free medium. The cells that overexpress PKB are then supertransfected with an expression vector that encodes MEK1. These cells are then adapted to growth in serum-free, protein-free medium.

What is claimed is:

1. An eukaryotic host cell genetically engineered to express a gene for a protein of interest, wherein the protein of interest is expressed as an extracellular product, and wherein the eukaryotic cell has been genetically engineered to also express a glut5 gene.

2. The host cell of claim 1 wherein the host cell is genetically engineered to express a second IGF-1-signaling pathway gene selected from the group consisting of a glut1 gene, an ERK1 gene, an ERK2 gene, a JNK gene, a 14-3-3 protein gene, an IRS gene, and a PI3 kinase gene.

3. The host cell of claim 2 wherein the glut5 gene is expressed under control of a heterologous regulatory element.

4. The host cell of claim 3, wherein the heterologous regulatory element is a viral promoter.

5. The host cell of claim 4, wherein the viral promoter is selected from the group consisting of a CMV promoter, an SV40 promoter, an RSV promoter and an adenoviral promoter.

6. The host cell of claim 1, wherein the protein of interest is selected from the group consisting of a soluble TNF receptor, a soluble IL-4 receptor, a soluble IL-1 type II receptor, a soluble Flt3 ligand, a soluble CD40 ligand, CD39, CD30, CD27, a TEK/Ork, IL-15, a soluble IL-15 receptor, Ox 40, GM-CSF, RANKL, RANK, TRAIL, a soluble TRAIL receptor, tissue plasminogen activator, Factor VIII, Factor IX, apolipoprotein E, apolipoprotein A-I, an IL-2 receptor, an IL-2 antagonist, alpha-1 antitrypsin, calcitonin, growth hormone, insulin, insulinotropin, insulin-like growth factors, parathyroid hormone, interferons, superoxide dismutase, glucagon, an erythropoeitin, an antibody, glucocerebrosidase, an Fc-fusion protein, a globin, a nerve growth factor, an interleukin, and a colony stimulating factor.

7. The host cell of claim 1, wherein the host cell is further genetically engineered to express a first selectable marker.

8. The host cell of claim 7, wherein the gene encoding the selectable marker is adjacent to the glut5 gene.

9. The host cell of claim 1, wherein the host cell is a mammalian cell.

10. The host cell of claim 9, wherein the host cell is selected from the group consisting of CHO, VERO, BHK, HeLa, CV1, MDCK, 293, 3T3, myeloma, PC12 and WI38 cells.

11. The host cell of claim 1, wherein the host cell is adapted to grow in serum-free medium.

12. The host cell of claim 11, wherein the host cell is a CHO.

13. A method of producing a protein of interest, the method comprising culturing the eukaryotic host cell of claim 1 under conditions such that the protein of interest is expressed.

14. The method of claim 13, wherein the host cell is genetically engineered to express a second IGF-1-signaling pathway gene selected from the group consisting of a glut1 gene, an ERK1 gene, an ERK2 gene, a JNK gene, a 14-3-3 protein gene, an IRS-1 gene, and a PI3 kinase gene.

15. The method of claim 13, further comprising collecting the protein of interest.

16. The method of claim 13, wherein the IGF-1-signaling pathway gene is expressed under control of a heterologous regulatory element.

17. The method of claim 16, wherein the heterologous regulatory element is a viral promoter.

18. The method of claim 17, wherein the viral promoter is selected from the group consisting of a CMV promoter, an SV40 promoter, an RSV promoter and an adenoviral promoter.

19. The method of claim 13, wherein the protein of interest is selected from the group consisting of a soluble TNF receptor, a soluble IL-4 receptor, a soluble IL-1 type II receptor, a soluble Flt3 ligand, a soluble CD40 ligand, CD39, CD30, CD27, a TEK/Ork, IL-15, a soluble IL-15 receptor, Ox 40, GM-CSF, RANKL, RANK, TRAIL, a soluble TRAIL receptor, tissue plasminogen activator, Factor VIII, Factor IX, apolipoprotein E, apolipoprotein A-I, an IL-2 receptor, an IL-2 antagonist, alpha-1 antitrypsin, calcitonin, growth hormone, insulin, insulinotropin, insulin-like growth factors, parathyroid hormone, interferons, superoxide dismutase, glucagon, an erythropoeitin, an antibody, glucocerebrosidase, an Fc-fusion protein, a globin, a nerve growth factor, an interleukin, and a colony stimulating factor.

20. The method of claim 13, wherein the host cell is further genetically engineered to express a first selectable marker.

21. The method of claim 20, wherein the gene encoding the selectable marker is adjacent to the glut5 gene.

22. The method of claim 13, wherein the host cell is a mammalian cell.

23. The method of claim 22, wherein the host cell is selected from the group consisting of CHO, VERO, BHK, HeLa, CV1, MDCK, 293, 3T3, myeloma, PC12 and WI38 cells.

24. The method of claim 13, wherein the host cell is cultured in serum-free medium.

25. The method of claim 24, wherein the medium is growth-factor free.

26. The method of claim 24, wherein the medium is protein-free.

27. The method of claim 26, wherein the medium is peptone-free.

28. The method of claim 13, wherein the host cell is a CHO cell.

29. A method of producing a mammalian cell line capable of growth in serum-free medium, the method comprising exposing cells that have been genetically engineered to overexpress a glut5 gene to serum-free medium, and isolating a cell line that grows in serum-free medium.

30. The method of claim 29, further comprising exposing the cells to peptone-free medium, and isolating a cell line that grows in peptone-free medium.

31. The method of claim 29, further comprising exposing the cells to protein-free medium, and isolating a cell line that grows in protein-free medium.

32. A method of producing an eukaryotic cell for production of a protein of interest, the method comprising genetically engineering an eukaryotic cell to express a protein of interest as an extracellular product, wherein the eukaryotic cell has been genetically engineered to also express a glut5 gene.

* * * * *

UNITED STATES PATENT AND TRADEMARK OFFICE
CERTIFICATE OF CORRECTION

| | |
|---|---|
| PATENT NO. | : 6,897,040 B2 |
| APPLICATION NO. | : 10/109971 |
| DATED | : May 24, 2005 |
| INVENTOR(S) | : Arvia E. Morris and Pranhitha Reddy |

It is certified that error appears in the above-identified patent and that said Letters Patent is hereby corrected as shown below:

In Column 3, line 12, "P13" should read -- Pl3 --.
In Column 10, line 57, "TL-3 should read -- IL-3 --.
In Column 13, line 33, "Stu1" should read -- Stul --.
In Column 13, line 34, "Sma1-Notl" should read -- Smal-Noti --.
In Column 22, line 25, "reombinant" should read -- recombinant --.

Signed and Sealed this

Seventh Day of August, 2007

JON W. DUDAS
*Director of the United States Patent and Trademark Office*